United States Patent
Bramlet

[11] Patent Number: 5,849,004
[45] Date of Patent: Dec. 15, 1998

[54] SURGICAL ANCHOR

[76] Inventor: Dale G. Bramlet, 2044 Brightwaters Blvd., St. Petersburg, Fla. 33704

[21] Appl. No.: 683,662

[22] Filed: Jul. 17, 1996

[51] Int. Cl.$^6$ .................................................. A61B 17/04
[52] U.S. Cl. ............................... 606/232; 606/72; 606/73
[58] Field of Search ............................... 606/232, 60, 72, 606/73, 75

[56] References Cited

U.S. PATENT DOCUMENTS

| | | |
|---|---|---|
| 3,374,786 | 3/1968 | Callender, Jr. . |
| 3,791,380 | 2/1974 | Dawidowski . |
| 3,892,232 | 7/1975 | Neufeld . |
| 4,009,712 | 3/1977 | Burstein et al. . |
| 4,237,875 | 12/1980 | Termanini . |
| 4,379,451 | 4/1983 | Getscher . |
| 4,409,974 | 10/1983 | Freedland . |
| 4,432,358 | 2/1984 | Fixel . |
| 4,488,543 | 12/1984 | Tornier . |
| 4,494,535 | 1/1985 | Haig . |
| 4,519,100 | 5/1985 | Wills et al. . |
| 4,561,432 | 12/1985 | Mazor . |
| 4,612,920 | 9/1986 | Lower . |
| 4,621,629 | 11/1986 | Koeneman . |
| 4,632,101 | 12/1986 | Freedland . |
| 4,653,489 | 3/1987 | Tronzo . |
| 4,657,001 | 4/1987 | Fixel . |
| 4,721,103 | 1/1988 | Freedland . |
| 4,759,352 | 7/1988 | Loxler . |
| 4,787,378 | 11/1988 | Sodhi . |
| 4,791,918 | 12/1988 | Von Hasselbach . |
| 4,964,403 | 10/1990 | Karas et al. . |
| 4,969,887 | 11/1990 | Sodhi . |
| 4,973,332 | 11/1990 | Kummer . |
| 4,973,333 | 11/1990 | Treharne . |
| 5,032,125 | 7/1991 | Durham et al. . |
| 5,041,114 | 8/1991 | Chapman et al. . |
| 5,041,116 | 8/1991 | Wilson . |
| 5,087,260 | 2/1992 | Fixel . |
| 5,098,433 | 3/1992 | Freedland . |
| 5,116,336 | 5/1992 | Frigg . |
| 5,129,901 | 7/1992 | Decoste . |
| 5,176,681 | 1/1993 | Lawes et al. . |
| 5,300,074 | 4/1994 | Frigg . |
| 5,356,410 | 10/1994 | Pennig . |
| 5,372,599 | 12/1994 | Martins . |
| 5,417,712 | 5/1995 | Whittaker et al. . |
| 5,429,641 | 7/1995 | Gotfried . |
| 5,437,674 | 8/1995 | Worcel et al. ............................. 606/73 |
| 5,456,721 | 10/1995 | Legrand . |
| 5,458,601 | 10/1995 | Young, Jr. et al. . |
| 5,472,452 | 12/1995 | Trott ........................................ 606/232 |
| 5,478,342 | 12/1995 | Kohrs ........................................ 606/73 |
| 5,489,210 | 2/1996 | Hanosh ..................................... 433/173 |
| 5,522,845 | 6/1996 | Wenstrom, Jr. ........................ 606/232 |
| 5,531,792 | 7/1996 | Huene ........................................ 623/16 |
| 5,571,104 | 11/1996 | Li .............................................. 606/72 |
| 5,643,321 | 7/1997 | McDevitt ................................ 606/232 |

Primary Examiner—Michael Buiz
Assistant Examiner—Tina T.D. Pham
Attorney, Agent, or Firm—Kenyon & Kenyon

[57] ABSTRACT

A surgical anchor useful in the repair or replacement of ligaments and/or tendons to associated human bone structure including an insert formed from a material that is biocompatible with human bone tissue and a series of fasteners carried by and which promote securement of the insert within the bone tissue. Each fastener carried by the insert is movable between retracted and extended positions. The surgical anchor furthermore includes a mechanism arranged in operable combination with and for positively moving the fasteners in either direction between their retracted and extended positions. The fasteners are preferably movable endwise relative to the insert.

51 Claims, 16 Drawing Sheets

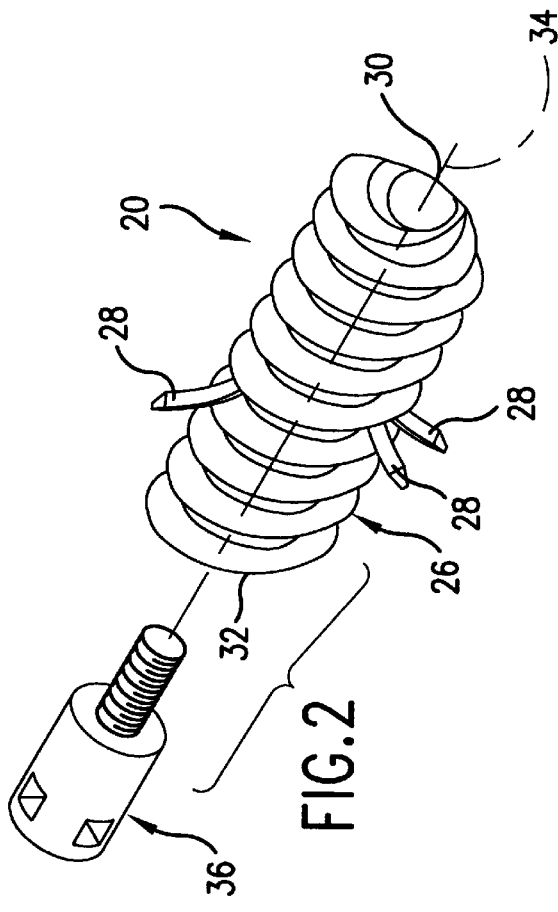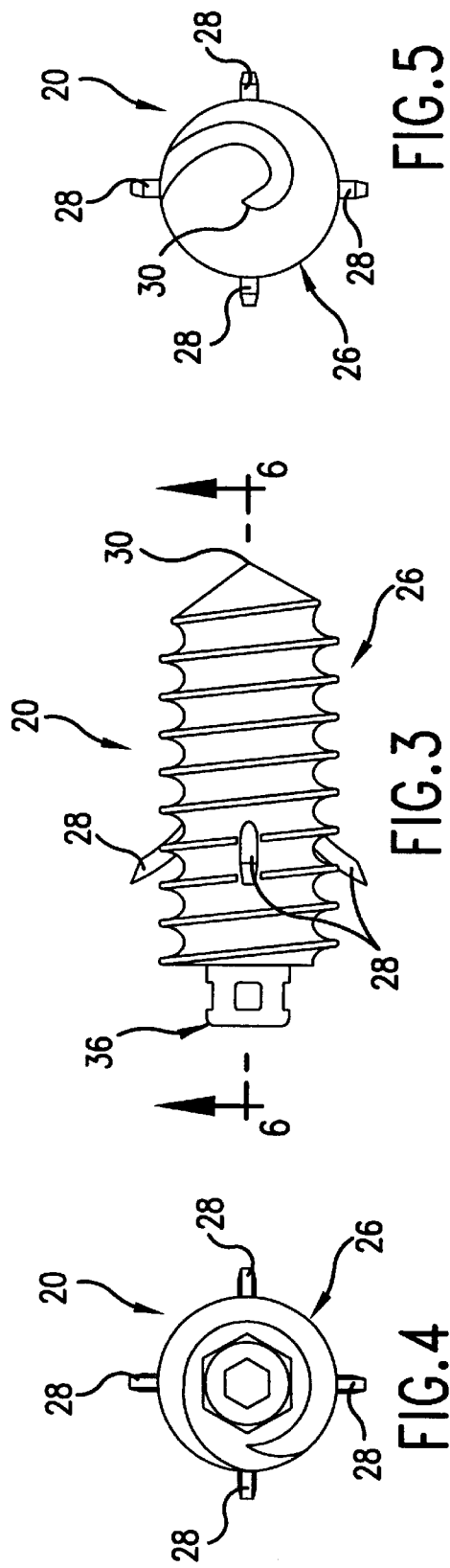

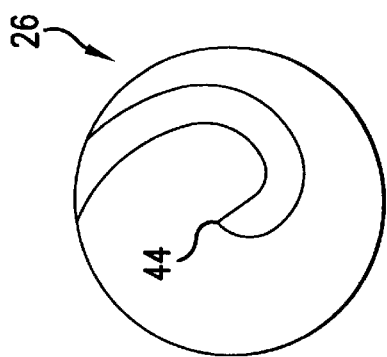
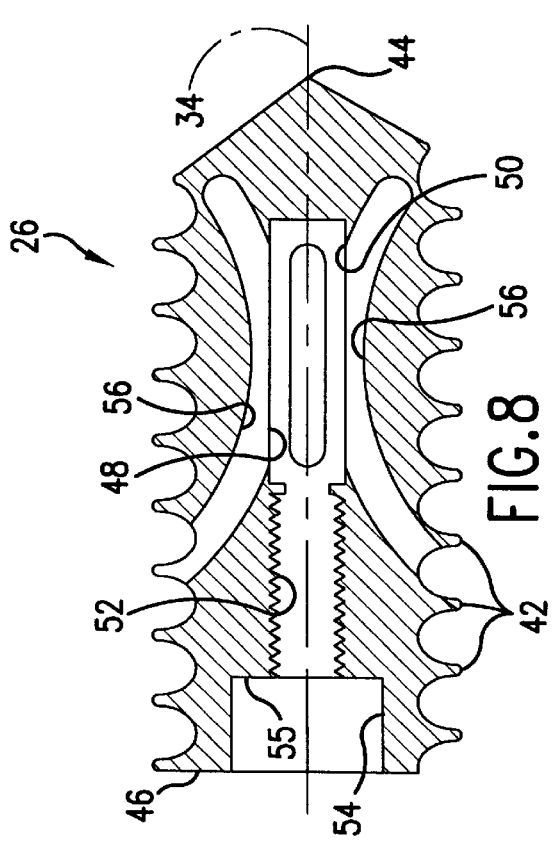
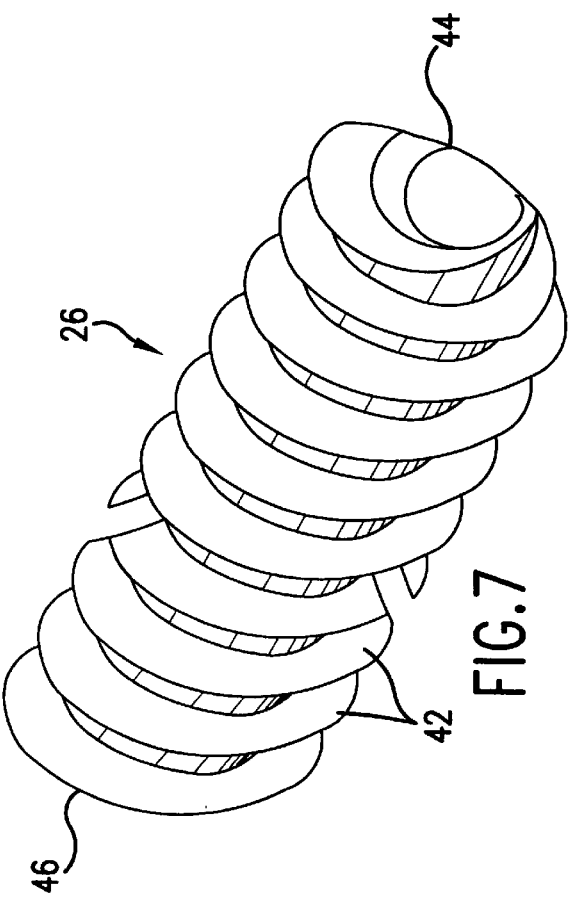
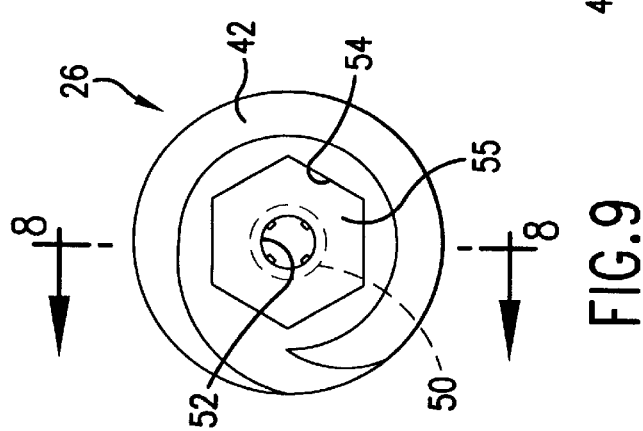

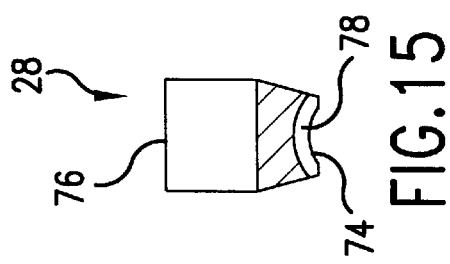
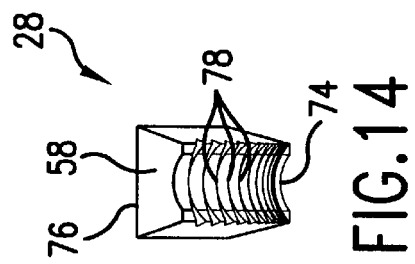
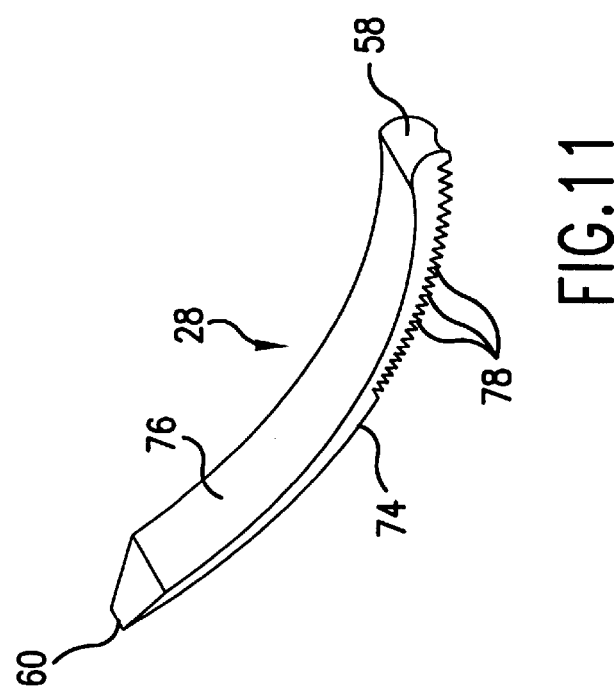
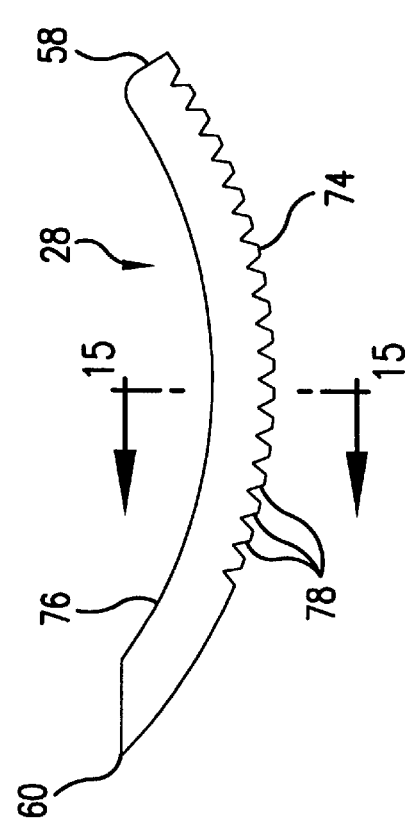
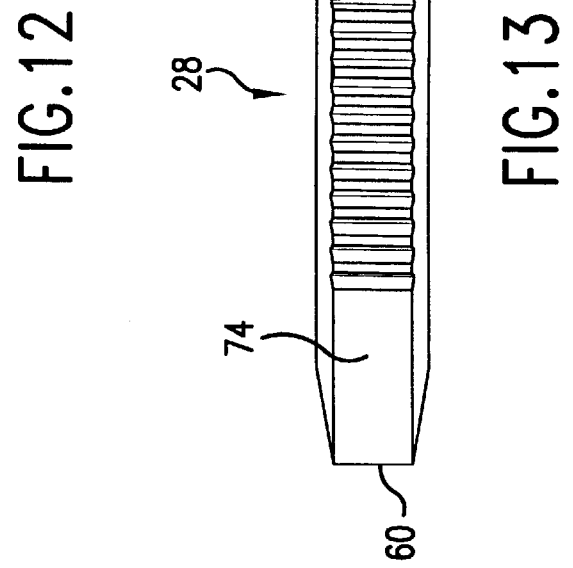

SURGICAL ANCHOR

FIELD OF THE INVENTION

The present invention generally relates to surgical anchors and, more particularly, to surgical anchors insertable within human bones for attaching objects thereto and having a series of fasteners that are positively displacable in opposite endwise directions.

BACKGROUND OF THE INVENTION

A relatively commonplace injury involves complete or partial separation of ligaments, tendons or other soft tissues from their associated human bones. Complete or partial separation of the ligaments, tendons and other soft tissue is relatively common place in athletes and typically result from excess stress being placed upon such tissue. Of course, soft tissue separation or detachment from human bone may likewise occur as a result of an accident such as a fall, over exertion during a work related activity, during the course of physical activity, or in several different situations involving human activity.

Given a sufficient time, and if particular care is taken to not reinjure the effected area or expose the injury to undue stress during the healing process, injuries involving partial detachment, which are commonly referred to as "sprains", often tend to heal themselves. On the other hand, if the ligament or tendon completely separates or detaches from the associated bone or bones, partial or permanent disability may occur. Moreover, if the ligament or tendon is severed as a result of a traumatic injury, partial or permanent disability may result. Accordingly, a number of surgical procedures have been devised for reattaching such detached or separated tissue. Moreover, surgical techniques have advanced such that severely damaged ligaments and/or tendons can now be replaced through surgery.

One such technique involves reattachment of the detached or separated tissue using "traditional" attachment devices such as metal staples, sutures over buttons, and cancellous bone screws. These "traditional" devices have also been used in connection with the attachment of ligaments or tendons that have been harvested from other parts of the human body and are being used to replace or repair severely damaged tissues. It should be appreciated, however, that "traditional" repair methods have not been uniformly successful. As an example, rigid attachment of ligaments and tendons using "traditional" attachment devices such as staples, screws and sutures cannot be maintained when extreme tensile loads are applied thereto.

Thus, there is a continuing need and desire for a surgical anchor that can be used to attach or reattach objects such as ligaments and/or tendons to an associated bone of a human being without requiring the use of bone plugs within a bone tunnel and which may lead to undesirable twisting of the ligament or tendon connected thereto.

SUMMARY OF THE INVENTION

In view of the above, and in accordance with the present invention, there is provided a surgical anchor useful in the repair or replacement of ligaments and/or tendons to associated human bone structure. The surgical anchor of the present invention comprises an elongated insert formed from a material that is biocompatible with human bone tissue. A series of fasteners are carried and promote securement of the insert within the bone tissue. Each fastener carried by the insert is movable between retracted and extended positions. When in their retracted position, the fasteners offer no operable anchoring effect to the insert within the bone tissue. When the fasteners are in their extended position, however, they extend outwardly from the insert while remaining in operable combination therewith to secure the insert within the bone substance. The present invention furthermore includes a mechanism arranged in operable combination with and for positively moving the fasteners from their retracted position to their extended position. Preferably, the fasteners are movable endwise relative to the insert. A salient feature of the present invention concerns the ability to operate the mechanism such that the fasteners can be positively retracted from their extended position to a retracted position to effect removal of the insert from the bone substance in those circumstances where it becomes necessary.

In a preferred form of the invention, the insert is configured with external threading extending axially along the insert to promote the securement of the insert within the bone substance. In this embodiment, the insert has a pointed leading end to facilitate engagement of the external threading with the bone substance. Moreover, a trailing end of the insert is configured to releasably accommodate a driving tool capable of imparting turning movements to the insert. In a most preferred form of the invention, the insert is formed from a material chosen from the class comprised of: titanium, a titanium alloy, stainless steel, or a cobalt chromium alloy.

The mechanism for moving the fasteners positively in opposite directions can be of any suitable type that is manually operated to allow the surgeon control over displacement of the fasteners. Preferably, the mechanism comprises a driver mounted for rotation within a cavity defined by the insert. The driver has external threading extending between opposite ends thereof. In the illustrated form of the invention, the external threading on the driver engages serrations on each of the fasteners whereby each fastener is endwise and positively displaced in either direction of travel depending upon the direction of rotation of the driver.

According to the illustrated embodiment of the invention, the insert defines a series of blind channels that are disposed about the periphery of the insert and with one end of each channel opening to the periphery of the insert. In a preferred form, each channel has a curvilinear configuration between opposite end thereof. Accordingly, each fastener has a corresponding curvilinear configuration between opposite ends thereof.

In a preferred from of the invention, the insert is configured toward one end to allow a portion of suture-like material to be fastened to the anchor thereby allowing a ligament or tendon to be connected with the suture-like material to the anchor. In one form of the invention, a ligament anchor is connected toward a trailing end of the insert. The ligament anchor is configured to allow a lengthwise portion of suture like material to be connected to the ligament anchor and thereby to the insert. Preferably, the ligament anchor includes an apertured head portion allowing the suture-like material to be connected thereto and a shank portion that threadably connects to the trailing end of the insert. Alternatively, the driver of the mechanism for imparting positive movement to the fasteners is configured to allow a lengthwise segment of suture-like material to be connected thereto.

With the present invention, the insert is fastened in the bone substance. In one form of the invention, the fasteners extending radially from the insert serve to secure the insert within the bone substance. Preferably, the insert is externally threaded to furthermore enhance its securement within the bone substance. Regardless of which embodiment is utilized, the insert of the present invention is configured to facilitate simple and convenient attachment of a ligament, tendon or other suitable human object thereto without danger of severing or twisting the ligament. Another salient feature of the present invention concerns providing a series of fasteners carried by the insert and which are operable in response to a mechanism, including a manually operated driver, that positively displaces the fasteners in opposite endwise directions. The ability to positively retract the fasteners facilitates purposeful removal of the insert from the bone tissue should that ever become necessary or required.

These and other objects, aims, and advantages of the present invention will become readily apparent from the following detailed description, the drawings, and the appended claims.

BRIEF DESCRIPTION OF THE DRAWINGS

FIG. 2 is a perspective view of one embodiment of the present invention;

FIG. 3 is a side elevational view of the invention shown in FIG. 2;

FIG. 4 is a left end view of the surgical anchor illustrated in FIG. 3;

FIG. 5 is a right end view of the surgical anchor illustrated in FIG. 3;

FIG. 7 is an enlarged perspective view of an insert forming part of the surgical anchor of the present invention;

FIG. 8 is a longitudinal sectional view of the insert illustrated in FIG. 7 taken along line 8—8 of FIG. 9;

FIG. 9 is a left end view of the insert shown in FIG. 8;

FIG. 10 is a right end view of the insert shown in FIG. 8;

FIG. 11 is an enlarged perspective view of a fastener forming part of the surgical anchor of the present invention;

FIG. 12 is a side elevational view of the fastener illustrated in FIG. 11;

FIG. 13 is a bottom elevational view of the fastener illustrated in FIG. 12;

FIG. 14 is a right end view of the fastener shown in FIG. 12;

FIG. 15 is a sectional view taken along line 15—15 of FIG. 12;

DETAILED DESCRIPTION OF THE PRESENT INVENTION

Figure 1:
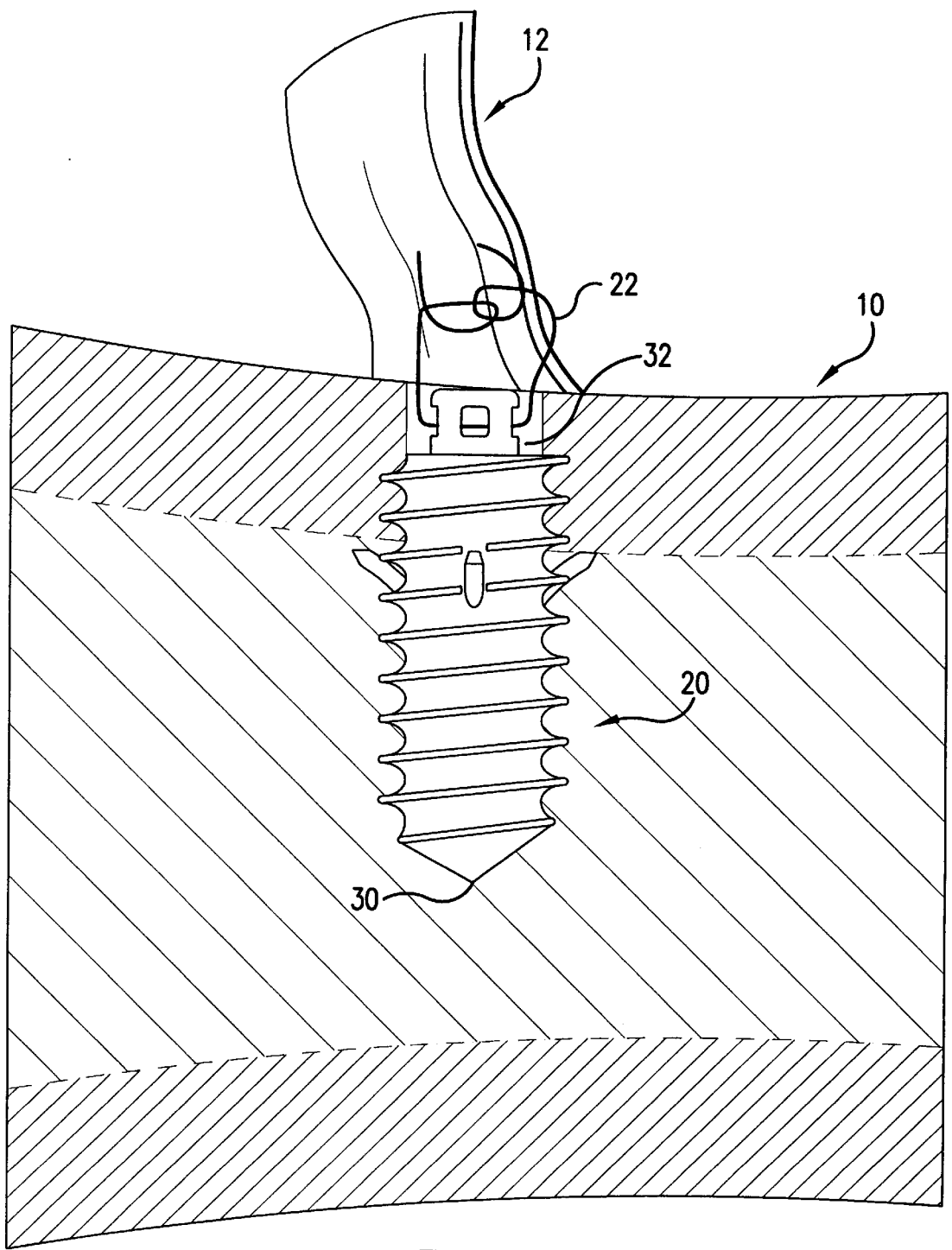
FIG. 1 is a view showing a portion of a bone having a surgical anchor according to the present invention inserted therewithin and having a series of fasteners extending radially outwardly from the insert and with a trailing end of the insert being attached to a ligament.

While the present invention is susceptible of embodiment in various forms, there is shown in the drawings and will hereinafter be described preferred embodiments of the invention with the understanding that the present disclosure is to be considered as setting forth exemplifications of the invention which are not intended to limit the invention to the specific embodiments illustrated.

Referring now to the drawings, wherein like reference numerals indicate like parts throughout the several views, there is schematically represented in FIG. 1 a portion of a bone 10 of a human being and a portion of an object 12, which can take many varied forms including a ligament or tendon, and that is anchored to the bone 10 as by a surgical anchor 20 formed in accordance with the present invention. Preferably, the object 12 is secured to the surgical anchor 20 as with suture-like material 22 and in a manner described in detail below.

One form of the present invention is illustrated in FIG. 2 through 5. As shown, the surgical anchor 20 preferably comprises an elongated insert 26 and a series of elongated pins or fasteners 28 carried by the insert 26 for endwise displacement relative thereto. As shown, one end 30 of the surgical anchor 20 is preferably pointed to facilitate insertion of the anchor 20 into the bone 10 (FIG. 1). An opposite end 32 of the surgical anchor 20 is configured to facilitate attachment of a lengthwise portion of the suture-like material 22 (FIG. 1) thereto thus promoting quick and easy securement of the ligament 12 to the bone 10. Moreover, the insert 26 defines an elongated or longitudinal axis 34 for the surgical anchor 20. In this form of the present invention, a ligament anchor 36 is operably associated with the trailing end 32 of the surgical anchor 20 to facilitate attachment of a lengthwise portion of suture-like material to the anchor 20.

Figure 6:
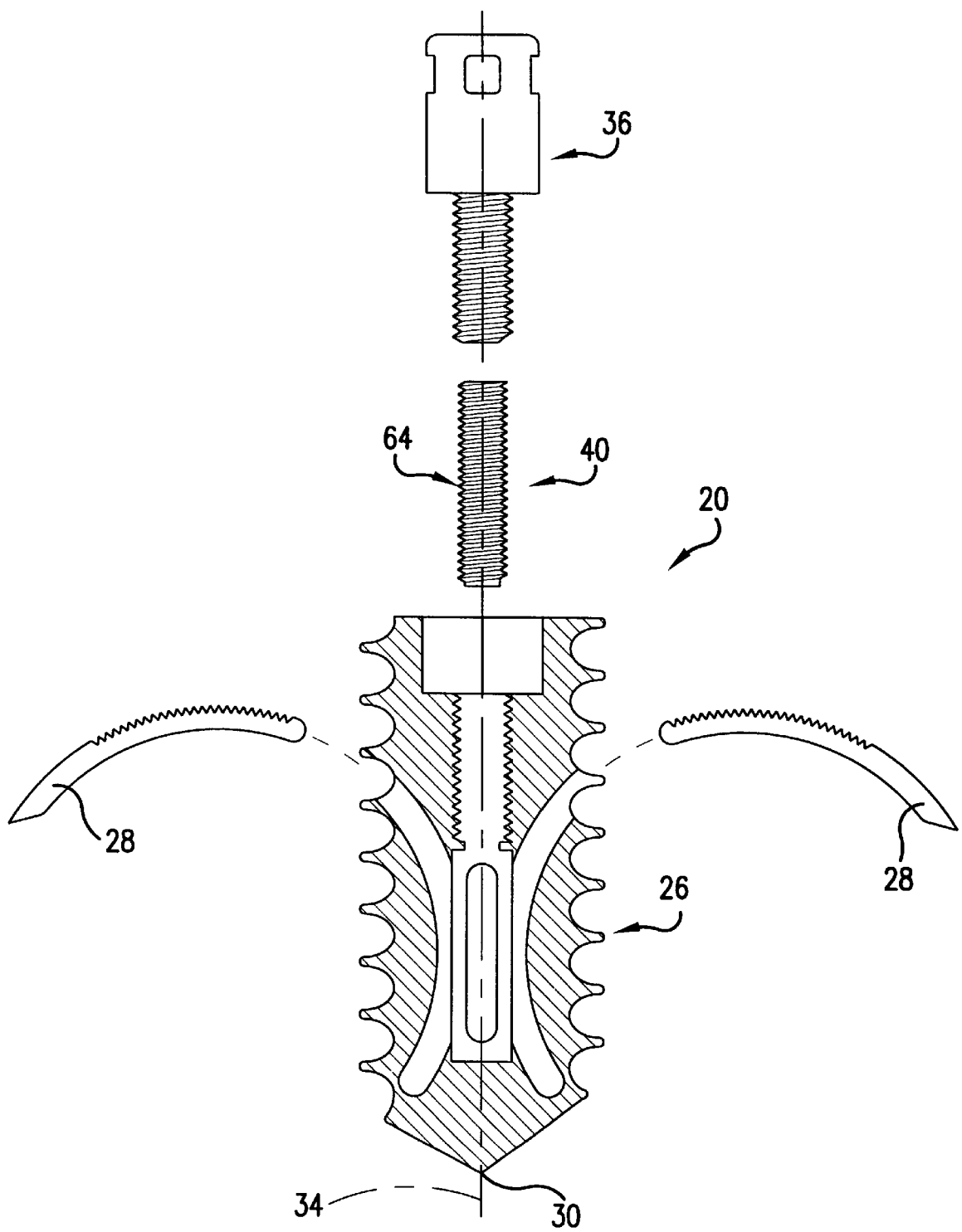
FIG. 6 is an exploded view, partially in longitudinal section, of that embodiment of the surgical anchor illustrated in FIG. 3.

As shown in FIG. 6, a salient feature of the present invention relates to the provision of a mechanism 40 for positively positioning the pins 28 relative to the surgical anchor 20. That is, and as will be described in detail below, the purpose of mechanism 40 is to positively extend the pins 28 outwardly from the insert 26 thereby enhancing securement of the surgical anchor 20 within the bone 10. Additionally, and in response to mechanical manipulation, the mechanism 40 furthermore operates to positively retract the pins 28 into the surgical anchor 20 thereby facilitating surgical removal of the surgical anchor 20 when desired or when found to be surgically necessary.

As will be appreciated by those skilled in the art, the exterior configuration of the insert 26 can take a myriad of shapes and forms. According to the present invention, and as illustrated in FIG. 7, the elongated insert 26 preferably has external threading 42 axially extending therealong between a generally pointed end 44 (FIG. 10) and a trailing end 46. As mentioned, the pointed configuration of the insert 26 promotes insertion and, in the illustrated embodiment, self-tapping of the surgical anchor 20 within the substance of bone 10 (FIG. 1). The external threading 42 along the exterior of the insert 26 has a relatively coarse pitch to enhance the purchasing ability and the anchorage of the anchor 20 within the substance of bone 10 (FIG. 1) in response to turning movements being imparted to the insert 26. Preferably, the insert 26 is formed from a material that is biocompatible with human bone tissue. In a most preferred form of the invention, the insert 26 is formed from a material chosen from the class comprised of: titanium, a titanium alloy, stainless steel, or a cobalt chromium alloy.

Turning to FIG. 8, the insert 26 defines an elongated axial bore 48 that opens to the trailing end 46 thereof. Preferably, the bore 48 defines an axially elongated blind cavity portion 50 arranged toward the leading end of the bore 48 and an internally threaded portion 52. The internally threaded portion 52 of bore 48 opens to the blind cavity portion 50 and to the trailing end 46 of the insert 26. Preferably, the internally threaded portion 52 of bore 48 has relatively fine pitched threading extending therealong.

The trailing end 46 of the insert 26 is preferably configured to releasably accommodate a driving tool (FIG. 24) capable of imparting turning movements to the insert 26. In a preferred form, and as shown in FIGS. 8 and 9, the trailing end of the axial bore 48 defined by insert 26 is suitably configured with a socket-like opening 54 for releasably accommodating a distal end of a driving tool. In a most preferred form of the invention, and as shown in FIG. 9, the socket or opening 54 has a hexagonal-like cross sectional configuration. It will be appreciated, however, that any suitable configuration including an elongated slot would equally suffice without detracting or departing from the spirit and scope of the present invention.

As shown in FIG. 8, the insert 26 further defines a series of axially elongated openings 56 arranged in spaced circumferential relation relative to each other. In the illustrated form of the invention, insert 26 is preferably provided with four generally equally spaced openings 56. Since the openings 56 are all substantially similar, only one opening 56 will be described in detail with the understanding that the other openings in the insert 26 are similar thereto. Each opening 56, intermediate opposite ends thereof, intersects with and opens to the blind cavity portion 50 of the axial bore 48 defined by insert 26. Preferably, the elongated openings 56 have a blind configuration but open at one end to the exterior of the insert 26. In the form of the invention illustrated in FIG. 8, each elongated opening 56 has a curvilinear or arcuate configuration between opposite ends thereof. That is, in the illustrated form of the invention, each opening 56 has an arcuate configuration having a predetermined and substantially constant radius.

An exemplary form of pin 28 is illustrated in FIGS. 11 through 15. Each pin 28 is shaped to slidably fit endwise within a respective one of the openings 56 (FIG. 8) formed in the insert 26. The shape and size of each pin 28 generally corresponds to the shape and size of an opening 56 defined by the insert 26. Preferably, each pin 28 is formed from a substantially rigid material that is biocompatible with the bone tissue of human beings. That is, the pin 28 should be configured with sufficient strength as to allow for insertion in and through the bone tissue without substantially bending intermediate opposite ends thereof. In a most preferred form of the invention, each pin 28 is formed from a material selected from the class comprised of: titanium, a titanium alloy, stainless steel, or a cobalt chromium alloy.

In the embodiment illustrated in FIGS. 11 through 13, each pin 28 has a leading end 58 and an opposite generally pointed end 60. Although the pin 28 is schematically illustrated as including a pointed end 60, it should be appreciated that any suitable shape for promoting insertion of the pin 28 into the substance of the bone will equally suffice. Intermediate its ends, each pin 28 preferably has a curvilinear or arcuate configuration. In the illustrated form of the invention, each pin 28 has a curved arc with a predetermined radius that is substantially equal to the predetermined radius of each opening 56 formed in insert 26 (FIG. 8) and which extends approximate to and outwardly away from the axis 34 of insert 26.

In a most preferred form of the invention, each pin 28 preferably forms an arc of about 80° between opposite ends thereof, and with the length of each pin 28 being selected such that when the leading end 58 of the pin 28 is fully retracted within the insert 26, the opposite pointed end 60 of the pin or barb 28 will be positioned within the outside diameter of the insert 26 to facilitate insertion of the surgical anchor 20 within the bone 10 (FIG. 1) of the patient. It is to be appreciated that the length of each barb or pin 28 is sized such that when the pins 28 are displaced to their extended position, the leading end 58 of each pin 28 remains operably associated with the insert 26 to allow for positive retraction of the pins 28 from their extended positions when desired or found necessary by the surgeon.

As mentioned above, the surgical anchor 20 of the present invention is further provided with a mechanism 40 for allowing positive displacement of the pins 28 in opposite directions relative to the insert 26. As will be appreciated, the mechanism for positively displacing the pins 28 in opposite direction can take a myriad of different forms without detracting or departing from the spirit and scope of the present invention. One mechanism which has proven advantageous and quite effective involves equipping the surgical anchor 20 with a manually operated driver 64 which is operably associated with the pins 28 such that upon manipulation of the driver 64, the pins 28 will be endwise displaced relative to the insert 26 thereby effecting the anchorage of the surgical anchor 20 within the bone 10.

Figure 16:
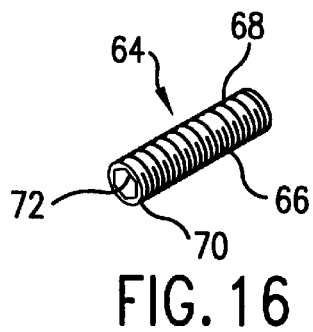
FIG. 16 is a perspective view of a driver forming part of that embodiment of the surgical anchor illustrated in FIG. 6.
Figure 18:
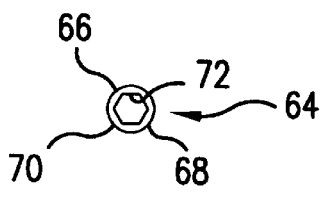
FIG. 18 is a left end view of the driver illustrated in FIG. 17.
Figure 17:
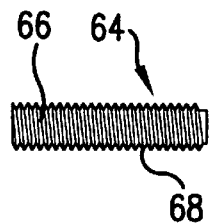
FIG. 17 is a side elevational view of the driver illustrated in FIG. 16.

FIGS. 16 through 18 illustrate a driver 64 for axially and positively displacing the pins 28 of the surgical anchor 20 in opposite directions relative to the insert 26. As shown, driver 64 comprises a member 66 having external threading 68 extending axially therealong. The driver member 66 is formed from a material that is biocompatible with bone tissue or substance and is preferably selected from the class comprised of: titanium, a titanium alloy, stainless steel, or a cobalt chromium alloy. It should be appreciated, however, other unnamed material would equally suffice without detracting or departing from the spirit and scope of the present invention. The outside diameter of the threaded member 66 is such that it slidably fits endwise through the internally threaded portion 52 of insert 26 (FIG. 8) and is accommodated for free rotation or turning movements in either rotational direction within the blind cavity portion 50 of insert 26. Preferably, the external threading 68 on member 66 has a relatively fine pitch thereto.

As shown in FIGS. 16 and 18, the trailing end 70 of the insert member 66 is preferably configured to releasably accommodate a driving tool (FIG. 25) capable of imparting turning movements to the insert member 66. In a preferred form, and as shown in FIGS. 16 and 18, the trailing end 70 of member 66 is suitably configured with a socket-like opening 72 for releasably accommodating a distal end of a driving tool. In a most preferred form of the invention, and as shown in FIGS. 16 and 18, the socket or opening 72 has a hexagonal-like cross sectional configuration. It will be appreciated, however, that any suitable configuration including an elongated slot would equally suffice without detracting or departing from the spirit and scope of the present invention.

As will be described hereinafter in detail below, the driver 64 of mechanism 40 is operably associated with each pin 28 such that manipulation of the driver 64 results in positive endwise displacement of the pins 28 either toward an extended or retracted positions depending upon the movements provided to the driver of mechanism 40. In the illustrated form of the invention, and returning now to FIGS. 11 through 15, each pin or barb 28 preferably has an inner surface 74, which proximates the axis 34 of the surgical anchor 20 when the pin 28 is inserted within insert 26, and an outer surface 76. As shown, the inner surface 74 of each pin 28 has a series of vertically slanted serrations 78 thereon. As will be appreciated from an understanding of this form of the invention, the serrations 78 act as threads and extend axially rearward from the leading end 58 for a lengthwise distance toward the pointed end 60 of each pin 28. Notably, the serrations 78 on each pin 28 are configured for threadable engagement with the exterior threading 68 extending axially along the outer surface of member 66. As such, the driver 64 of anchor 20 is operably engaged or associated with each of the pins 28 of the surgical anchor 20.

Figure 19:
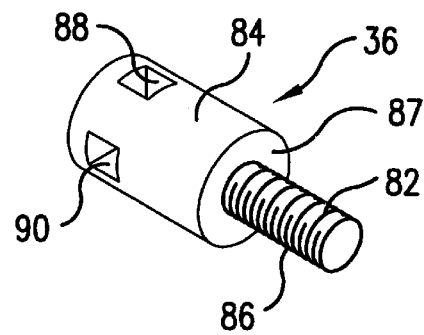
FIG. 19 is a perspective view of a ligament anchor forming part of that embodiment of the surgical anchor illustrated in FIG. 6.
Figure 21:
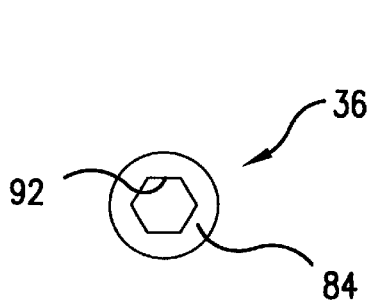
FIG. 21 is a left end view of the ligament anchor illustrated in FIG. 20.
Figure 20:
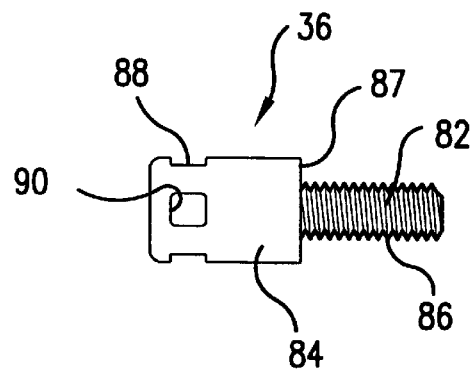
FIG. 20 is a side elevational view of the ligament anchor illustrated in FIG. 19.

FIGS. 19 through 21 illustrate one form of ligament anchor 36 that is utilized to facilitate quick and easy releasable attachment of a lengthwise portion of suture-like material 22 (FIG. 1) to the surgical anchor 20. The ligament anchor 36 is formed from a material that is biocompatible with bone tissue or substance and is preferably selected from the class comprised of: titanium, a titanium alloy, stainless steel, or a cobalt chromium alloy. It should be appreciated, however, other unnamed materials would equally suffice without detracting or departing from the spirit and scope of the present invention.

Suffice it to say, in the illustrated embodiment, the ligament anchor 36 comprises an axially elongated shank portion 82 that is rigidly connected in axial alignment to and turns with an axially elongated head portion 84. The shank portion 82 of ligament anchor 36 has external threading 86 extending therealong. Notably, the external threading 86 on shank portion 82 of ligament anchor 36 corresponds in pitch to the internally threaded portion 52 of the axial bore 48 of insert 26 (FIG. 8). As shown, in the particular embodiment illustrated, the head portion 84 of the ligament anchor has a larger diameter than is the external threading on the shank portion 82. Accordingly, a radial shoulder 87 is defined between the shank portion 82 of the ligament anchor 36 and the enlarged head portion 84. Moreover, the head portion 84 of the ligament anchor 36 has a series of throughbores 88 and 90 arranged in general normal relation relative to each other so as to allow a lengthwise portion of the suture-like material 22 (FIG. 1) to pass endwise therethrough.

Moreover, and as will be appreciated from an understanding of the present invention, the axial length of the head portion 84 of ligament anchor 36 can be altered from that illustrated without detracting or departing from the spirit and scope of the present invention. That is, during a surgery, a surgeon may have a collection of ligament anchors to select from; with each anchor 36 having a different length such that a proper relationship is maintained with the bone 10 of the patient. Furthermore, when an insert 26 having a socket-like opening 54 is selected for insertion within the bone 10 of the patient, the outer diameter of the head portion 84 of the ligament anchor 36 will be sized to fit within the socket-like opening 54 of the insert 26.

To facilitate insertion and ultimately connection of the ligament anchor 36 to the insert 26 (FIG. 3), the ligament anchor 36 is preferably provided with a configuration allowing a driving tool to be releasably connected thereto. In the illustrated embodiment, and as shown in FIG. 21, the head portion 84 of the ligament anchor 36 is provided with a tool accommodating recess 92. In the preferred form, the trailing end of the head portion 84 of ligament anchor 36 is suitably configured with a socket-like opening 92 for releasably accommodating a distal end of a driving tool. In a most preferred form of the invention, and as shown in FIG. 21, the socket or opening 92 has a hexagonal-like cross sectional configuration. It will be appreciated, however, that any suitable configuration including an elongated slot would equally suffice without detracting or departing from the spirit and scope of the present invention.

Figure 22:
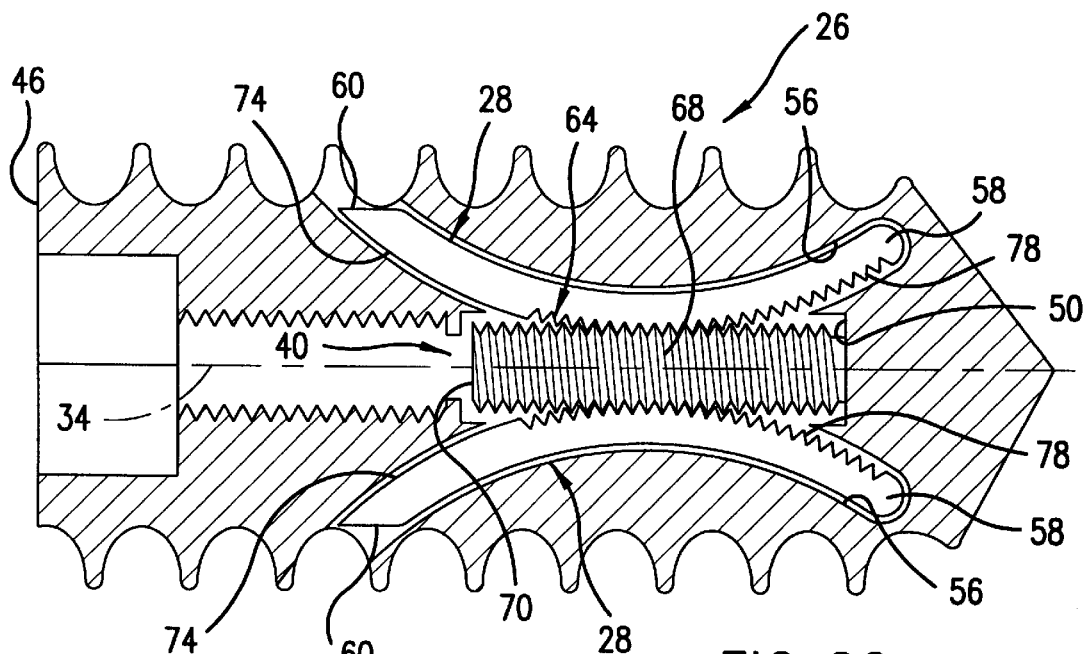
FIG. 22 is a longitudinal sectional view of the surgical anchor with the fasteners shown in a retracted position relative to the insert.

As shown in FIG. 22, the pins 28 slidably fit endwise within the openings 56 defined by the insert 26. In the illustrated form of the invention, the pointed ends 60 of the pins 28 extend toward a rear end 46 of the insert 26. Notably, in the illustrated form of the invention, a lengthwise portion of the inner surface 74 of each pin 28 protrudes into the blind cavity portion 50 defined by the insert 26. As such, the serrations 78 defined on the inner surface 74 of the pins 28 proximates the centerline or longitudinal axis 34 of the surgical anchor 40.

After the pins 28 are inserted within their respective openings 56 in the insert 26, the driver 64 of the operating mechanism 40 is operably connected to each of the pins 28. As shown in FIG. 22, as the driver 64 is inserted within the blind cavity 50 of the insert 26 it is also rotated such that the external threading 68 on the driver 64 operably engages with the serrations 78 on the pins 28 thereby establishing a positive drive connection therebetween. In the illustrated form of the invention, the openings 56 are preferably configured as blind openings. Thus, the leading ends 58 of the pins 28 are prevented from endwise passing out of the insert 26 as the driver 64 is connected in operable relationship therewith.

Figure 23:
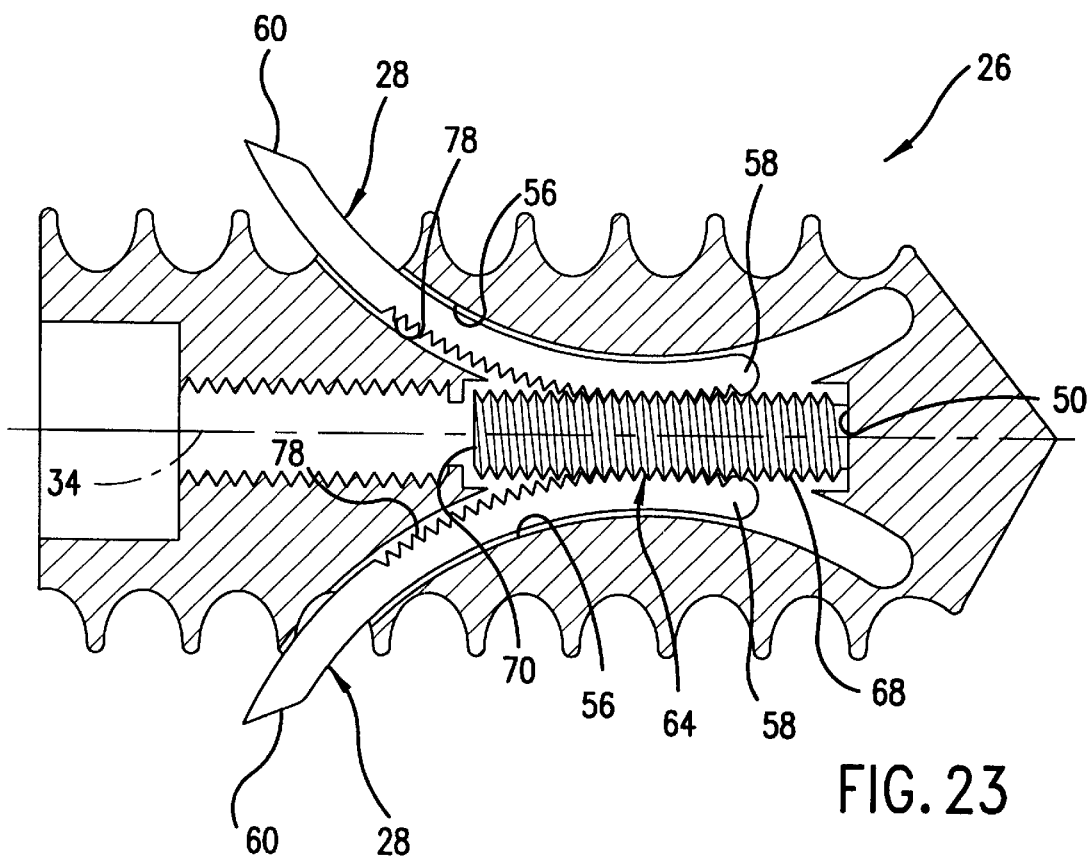
FIG. 23 is a longitudinal sectional view of the surgical anchor, similar to FIG. 22, but showing the fasteners in an extended position relative to the insert.

As shown in FIG. 23, an opposite end of each opening 56 defined by insert 26 for accommodating a pin 28 opens to the exterior surface of the insert 26. Accordingly, manual manipulation of the manually operated mechanism 40 will forcibly propel the pointed end 60 of each pin 28 through the open end of its opening 56 in a direction radially outward from axis 34 of the surgical anchor 20.

Figure 24:
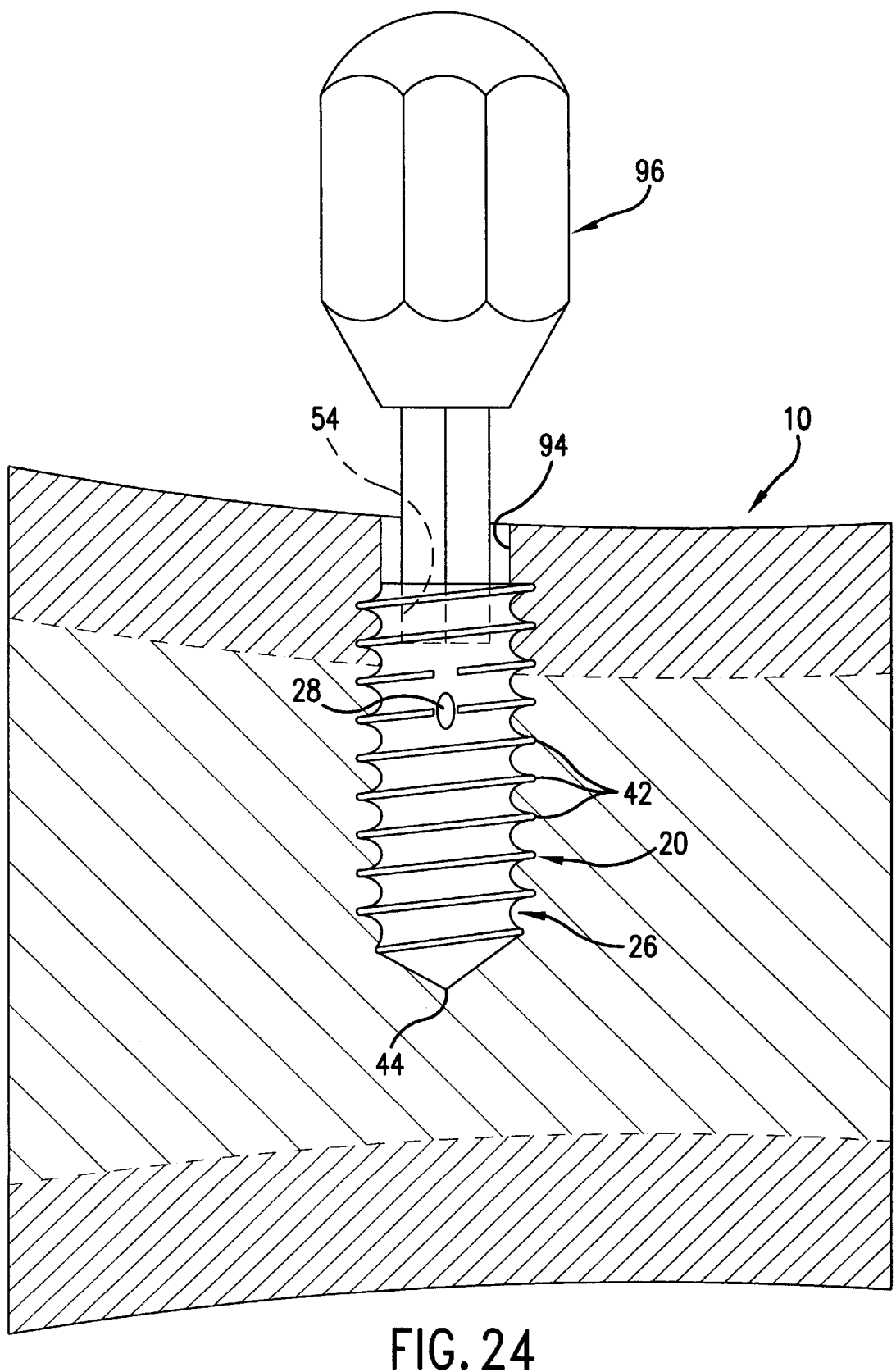
FIG. 24 is a schematic representation of the insert of,the surgical anchor being longitudinally inserted into human bone tissue.

Prior to insertion of the surgical anchor 20 into a bone 10 (FIG. 1) of a patient, the pins 28 are arranged in the position shown in FIG. 22 with the driver 64 of the drive mechanism preferably arranged in operable association with each pin 28. As shown in FIG. 24, a recess or bore 94 is drilled or otherwise provided in the bone 10 of the patient. The insert 26 assembled with pins 28 is then endwise inserted into the bore 94 preferably with the pointed end 44 of the insert 26 being initially inserted into the bore 94. In the preferred form of the invention, a distal end of a suitable driving tool 96 is inserted into the socket-like opening 54 in the insert 26. Thereafter, the tool 96 and thereby the insert 26 is turned such that the external threading 42 on the insert 26 engages with the bone substance thereby enhancing securement of the surgical anchor 20 within the bone 10.

Figure 25:
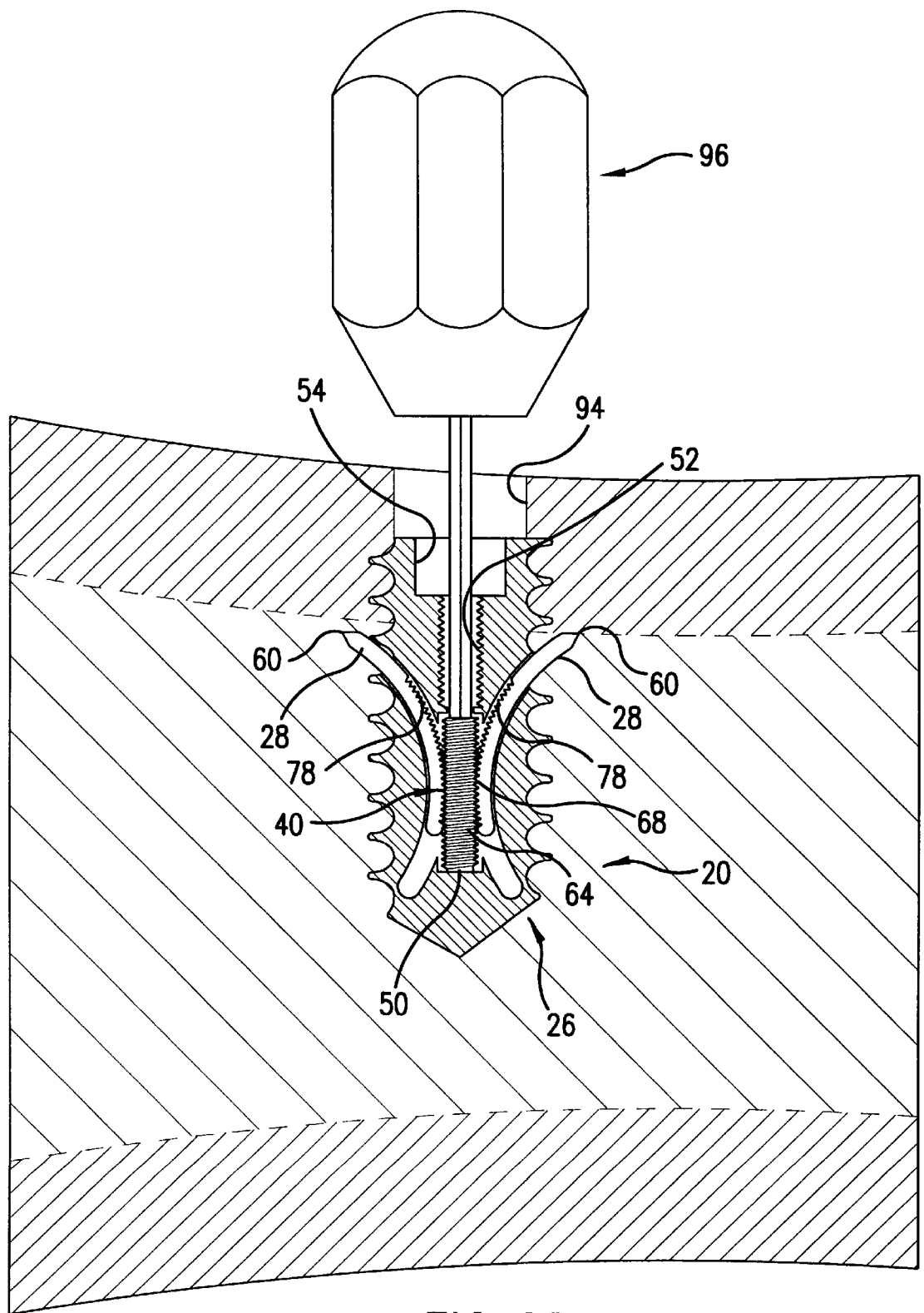
FIG. 25 is a longitudinal sectional view similar to FIG. 24 but showing distention of the fasteners radially outward from the insert.

After the insert 26 is inserted into the bore 94, and as shown in FIG. 25, mechanism 40 is operated to positively distend the pins 28 radially outwardly relative to the insert 26 to enhance securement of the surgical anchor 20 within the bone 10. In the illustrated embodiment of the invention, the driver 64 of mechanism 40 is operated to forcibly move the pins 28 axially and outwardly relative to the insert 26 and into engagement with the bone substance. As will be appreciated, the pointed configuration 60 of the pins 28 facilitates endwise movement of the pins 28 into securement with the bone substance. In the illustrated form of the invention, a distal end of a driving tool 96 is sized to pass endwise through the socket like portion 54 and the internally threaded portion 52 of the insert 26 and into operable driving engagement with the socket like opening 72 (FIGS. 16 and 18) in the driver 64.

In this form of the invention, the driver 64 is positioned for free rotation within the blind cavity portion 50 of the insert 26. As such, turning movements imparted to the driver 64 through tool 96 will result in positive endwise displacement of the pins 28 relative to the insert as through the threaded engagement of the external threading 68 on the driver 64 and the slanted or inclined serrations 78 on the pins 28. Of course, and as should be appreciated, the endwise displacement of the pins 28 relative to the insert 26 will be a function of the direction of rotation imparted to the driver 64. That is, a salient feature of the present invention is that the mechanism 40 associated with the surgical anchor 20 can endwise displace the pins 28 in opposite or both endwise directions. In the illustrated form of mechanism 40, after the pins 28 are extended into the bone substance, a lengthwise portion of each pin 28 remains operably associated with the driver 64 (FIG. 25) of mechanism 40 such that reverse rotation of the driver 64 will positively effect retraction of the pins 28 relative to the surgical anchor 20.

Figure 26:
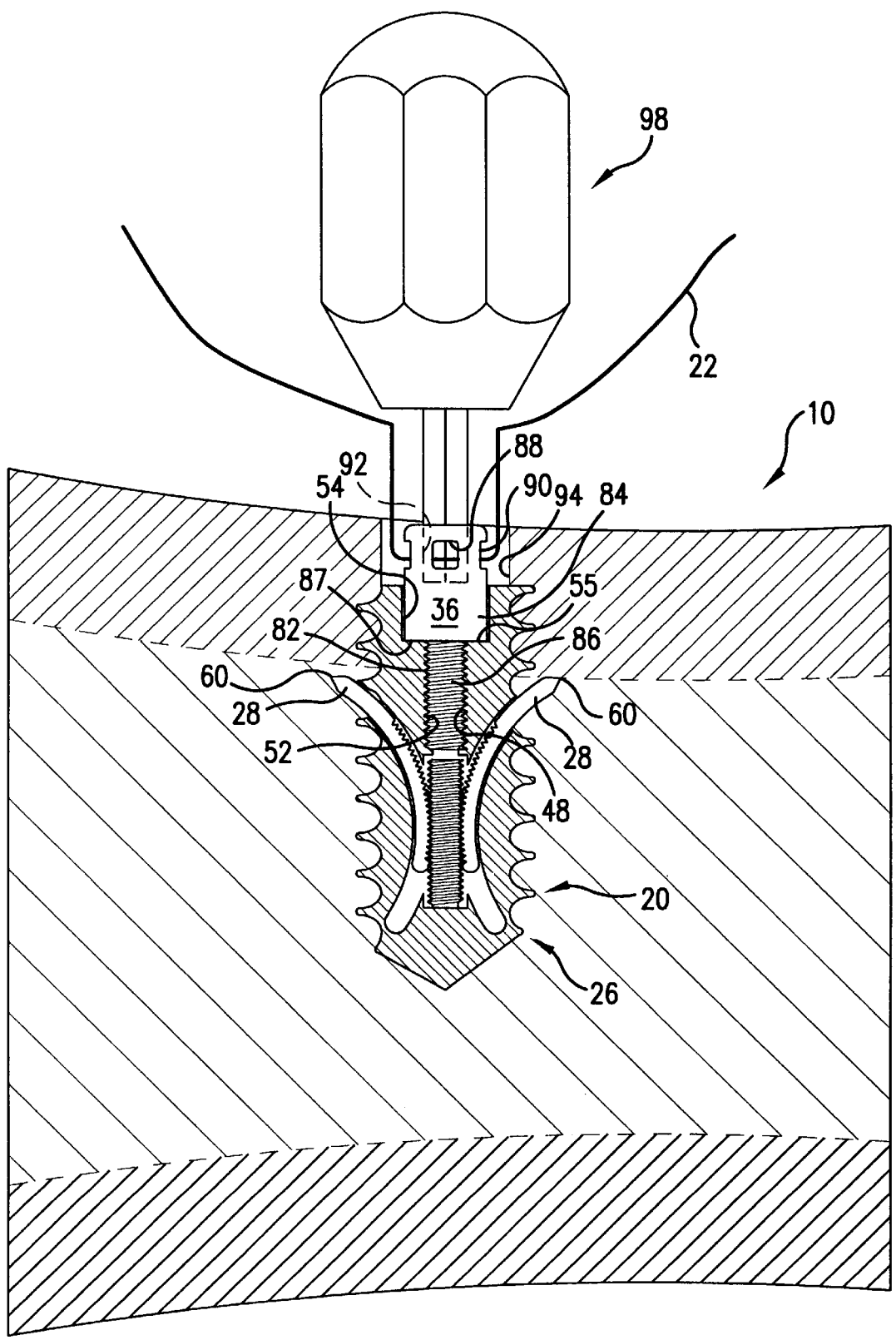
FIG. 26 is a longitudinal sectional view similar to FIG. 25 but showing a ligament anchor connected to a trailing end of the insert and with a lengthwise segment of suture-like material extending through the ligament anchor.

Turning to FIG. 26, after the pins 28 are positioned to secure the surgical anchor 20 within the bore 94 in the bone 10, the ligament anchor 36 is connected to the insert 26. As seen in FIG. 26, a suitable tool 98 is used to connect the ligament anchor 36 to the insert 26. As shown, the external threading 86 on the shank portion 82 of the ligament anchor 36 preferably engages with the internal threaded portion 52 of the axial bore 48 defined by insert 26. Thereafter, a distal end of tool 98 is releasably received in the tool accommodating recess 92 defined by the head portion 84 such that turning movements can be imparted to ligament anchor 36 thereby allowing the external threading 86 on the shank portion 82 to threadably engage with the internally threaded portion 52 of axial bore 48.

Figure 27:
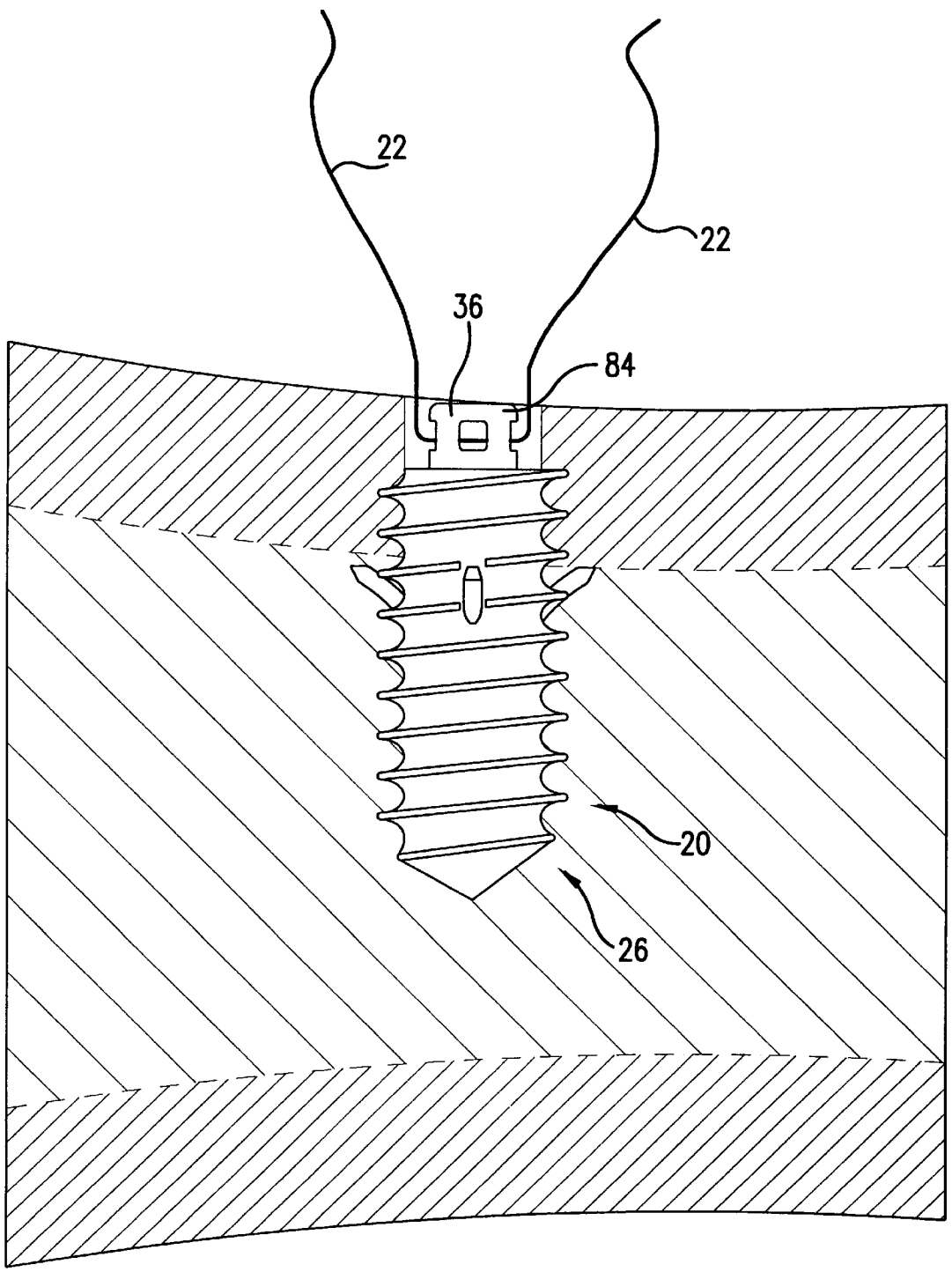
FIG. 27 is a view similar to FIG. 26.

Preferably, turning movements are imparted by tool 98 to the ligament anchor 36 until the radial shoulder 87 on the ligament anchor 36 engages with the step 55 defined by insert 26 thereby limiting further endwise movement of the ligament anchor 36 toward the insert 26. Notably, as the ligament anchor 36 is connected to the insert 26, the head portion 84 thereof is preferably sized to fit endwise within the socket-like opening 54 defined by the insert 26. Moreover, and as shown in FIG. 27, the head portion 84 of the ligament anchor 36 is specifically sized such that when it is secured to the insert 26, the trailing end of the head portion 84 preferably does not extend or project beyond the outer surface of the bone 10.

After the ligament anchor 36 is secured to the insert 26, a lengthwise portion of suture-like material 22 is passed endwise through the apertures or throughbores 88 and 90. As shown in FIG. 1, the suture-like material 22 is ultimately used to secure an object such as a ligament or tendon 12 to the bone 10.

Figure 28:
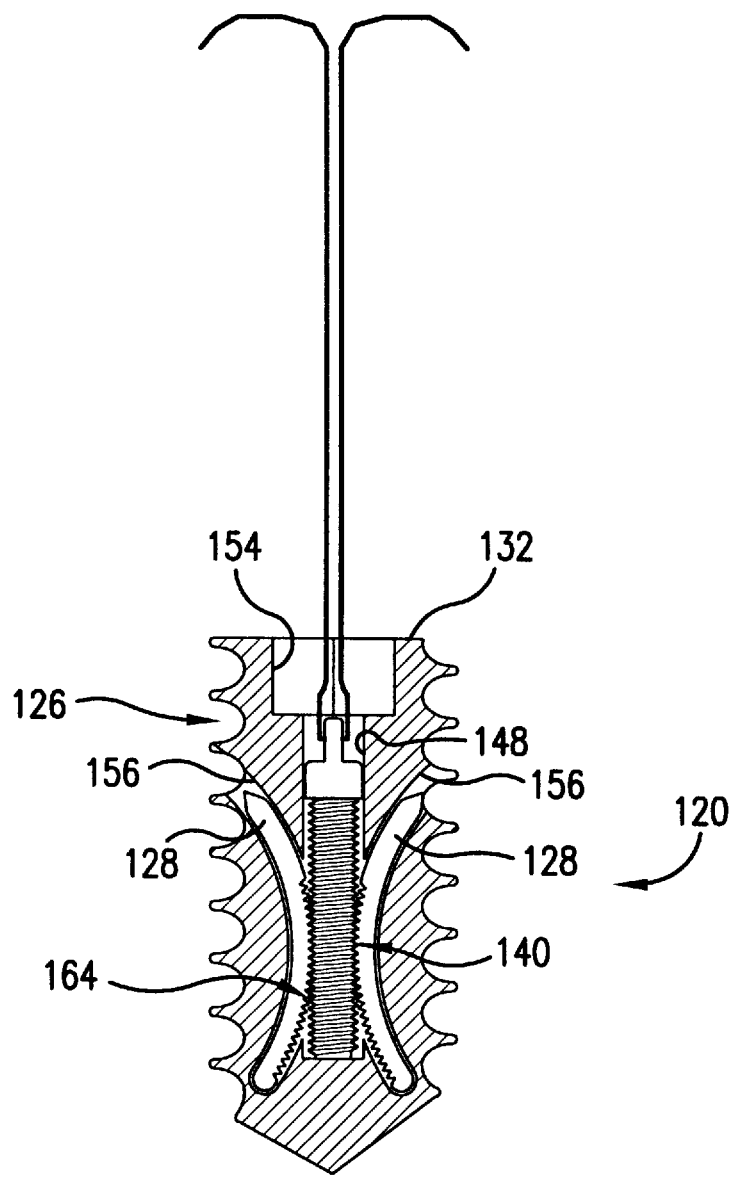
FIG. 28 is a longitudinal sectional view of an alternative embodiment of the present invention.
Figure 29:
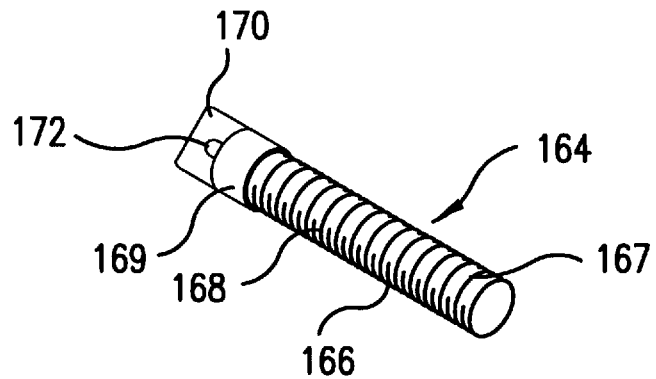
FIG. 29 is a perspective view of an alternative form of driver to be used in combination with the alternative embodiment of the surgical anchor illustrated in FIG. 28.

Another embodiment of surgical anchor according to the present invention is shown in FIG. 28. The alternative form of surgical anchor shown in FIG. 28 is designated generally by reference numeral 120. The elements of this alternative form of surgical anchor that are identical to or functionally analogous to those components mentioned above with respect to surgical anchor 20 are designated by reference numerals identical to those used above with the exception that this embodiment uses reference numeral in the 100 series.

In this embodiment of the invention, the insert 126 and pins 128 are substantially similar to that discussed above. As mentioned above, the insert 126 includes an elongated axial bore 148 and a series of evenly spaced openings 156 that accommodate the pins 128 for endwise movements. Intermediate their ends, and as discussed above, the openings 156 open to the axial bore 148 defined by insert 126. The bore 148 defined by insert 126 is preferably configured as a blind bore that opens to a trailing end 132 of insert 126. Unlike that mentioned above, however, bore 148 has no internal threading extending along the length thereof.

Preferably, insert 126 has a socket-like portion opening 154 toward that end of the bore 148 that opens to the trailing end 132 of the insert 126. The opening 154 preferably has a configuration similar to the socket-like opening 54 discussed above but it should be appreciated that any suitable opening for releasably accommodating a driving tool capable of imparting turning movements to the surgical anchor 120 would equally suffice.

The surgical anchor 120 further includes a drive mechanism 140 for positively displacing the pins or barbs 128 in opposite directions between retracted and extended positions and relative to the insert 126. The drive mechanism 140 is arranged in operable relationship with the pins 128 regardless of the disposition of the pins or barbs 128 relative to the insert 126. As such, the pins 128 can be positively displaced relative to the insert in opposite directions.

In the illustrated form of the invention, drive mechanism 140 includes a driver 164 for positively displacing the pins 128 in opposite directions between retracted and extended positions and relative to the insert 126. As with the first embodiment of the invention, the driver 164 is operably associated with each of the pins 128. Accordingly, actuation of the driver 164 results in endwise displacement of the pins 128 relative to insert 126. The operable association of driver 164 relative to pins 128 is substantially similar to that between driver 64 and pins 28 but it should be appreciated that other drive arrangements for effecting endwise and positive displacement of the pins 128 relative to the insert 126 remain within the spirit and scope of the present invention.

As shown in FIGS. 29 through 32, driver 164 preferably includes an elongated member 166 with threading 168 extending axially along the exterior thereof. The elongated member 166 is formed form a material that is biocompatible with the bone tissue and is preferably selected form the class of materials comprised of: titanium, a titanium alloy, stainless steel, or a cobalt chromium alloy. It should be appreciated, however, that other unnamed materials would equally suffice without detracting or departing from the spirit and scope of the present invention. The outside diameter of the threaded member 166 is such that it slidably fits endwise through the axial bore 148 defined by insert 126 (FIG. 28).

As shown for illustrative purposes in FIGS. 29 through 32, drive member 166 includes an elongated shank portion 167 with a head portion 169 arranged at a trailing end of the drive member 166. In this form of the invention, the shank portion 167 of drive member 166 has the external threading 168 extending axially therealong. The external threading 168 of drive member 166 has a relatively fine pitch that is complementary to serrations or threading 178 on the inner surface 174 of pins 128.

Figure 30:
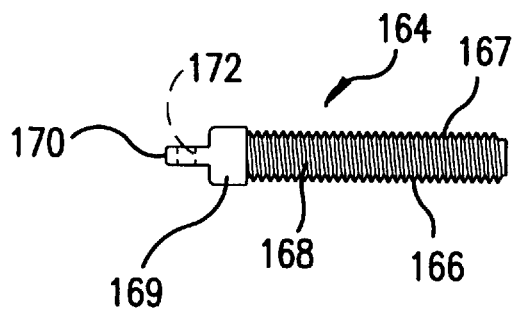
FIG. 30 is a side view of the driver illustrated in FIG. 29.
Figure 31:
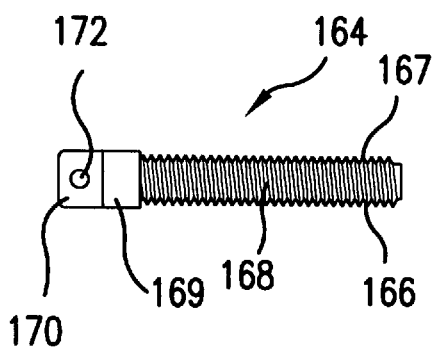
FIG. 31 is another side view of the driver illustrated in FIG. 29.
Figure 32:
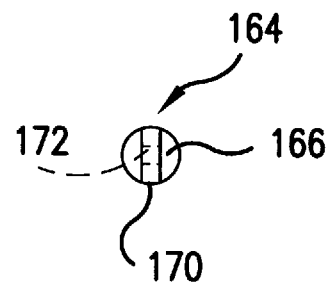
FIG. 32 is a left end view of the driver illustrated in FIG. 31.

The head portion 169 of drive member 166 is configured to releasably accommodate a driving tool capable of imparting turning movements to the driver 164. In the illustrated embodiment, the head portion 169 of the drive member 166 includes an axial projection 170 extending from a trailing end of the head portion 169 of drive member 166. As shown in FIGS. 30 through 32, the axial projection 170 preferably has a flat blade-like configuration defining an aperture or opening 172 for allowing a lengthwise portion of suture-like material to be captively passed therethrough.

Figure 33:
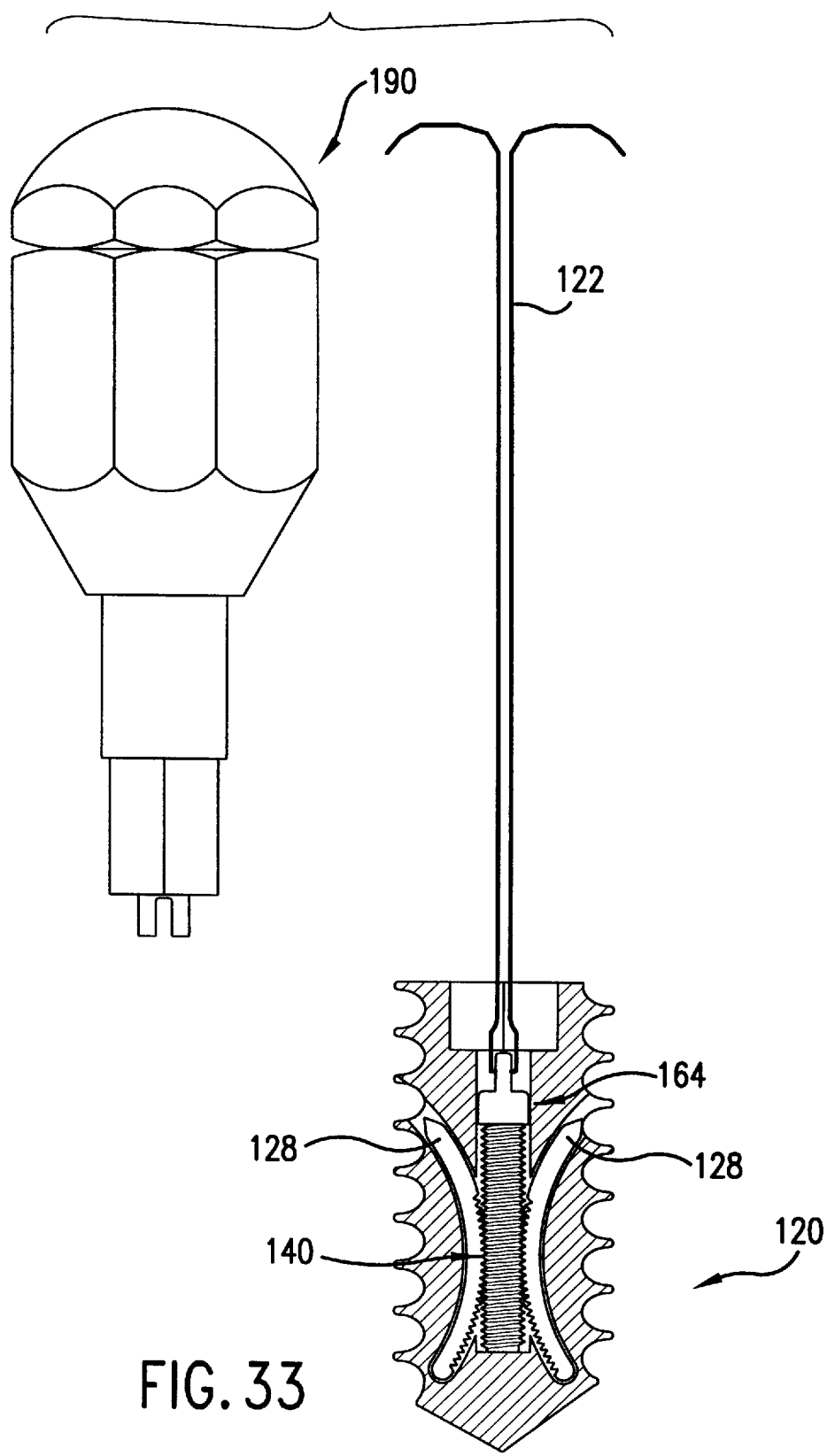
FIG. 33 is a view similar to FIG. 28 but showing a tool to be sued in combination with the alternative embodiment of the surgical anchor shown in FIG. 28.
Figure 34:
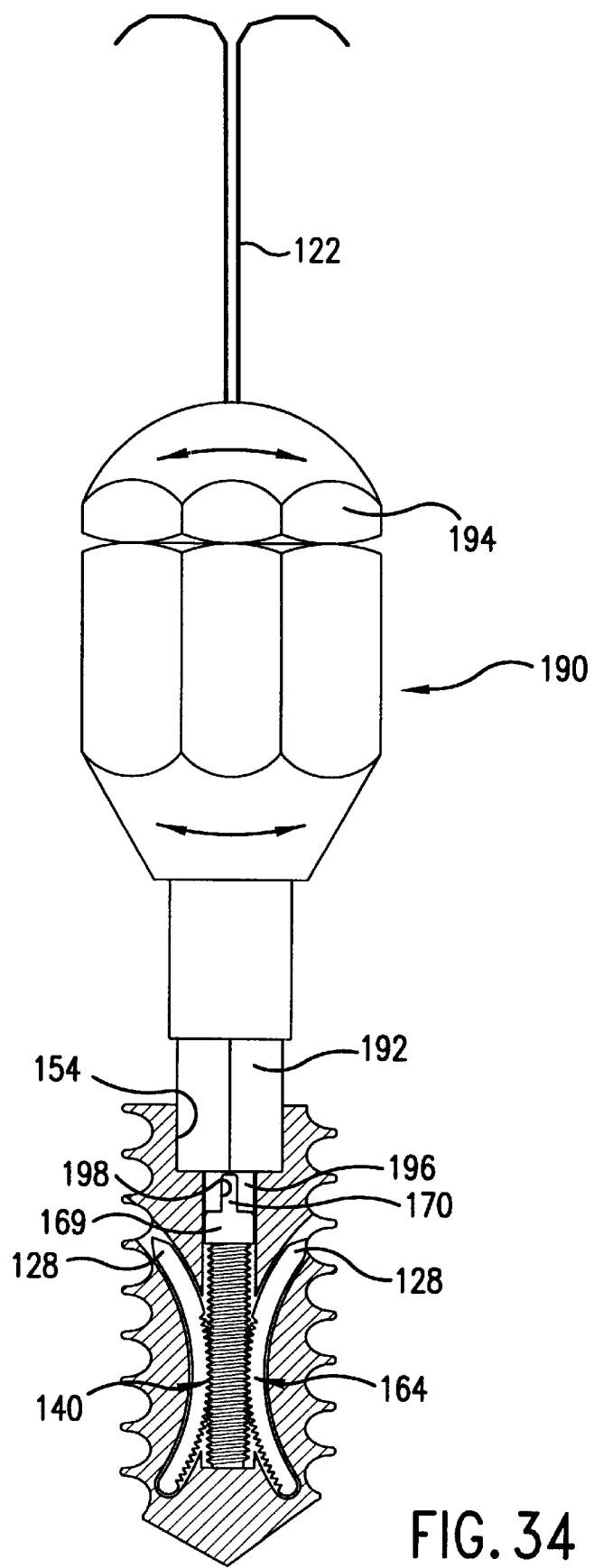
FIG. 34 is a view similar to FIG. 33 but showing the tool arranged in operable combination with the surgical anchor and with a suture-like material extending endwise through the tool.

As mentioned above, prior to insertion of the surgical anchor 120 into the patient, the pins 128 are preferably arranged in position shown in FIG. 33, with the driver 164 of mechanism 140 preferably arranged in operable association with each pin or fastener 128. As shown in FIG. 34, a distal end of a suitable driving tool 190 is inserted into the socket-like opening 154 to facilitate insertion of the surgical anchor 120.

Figure 35:
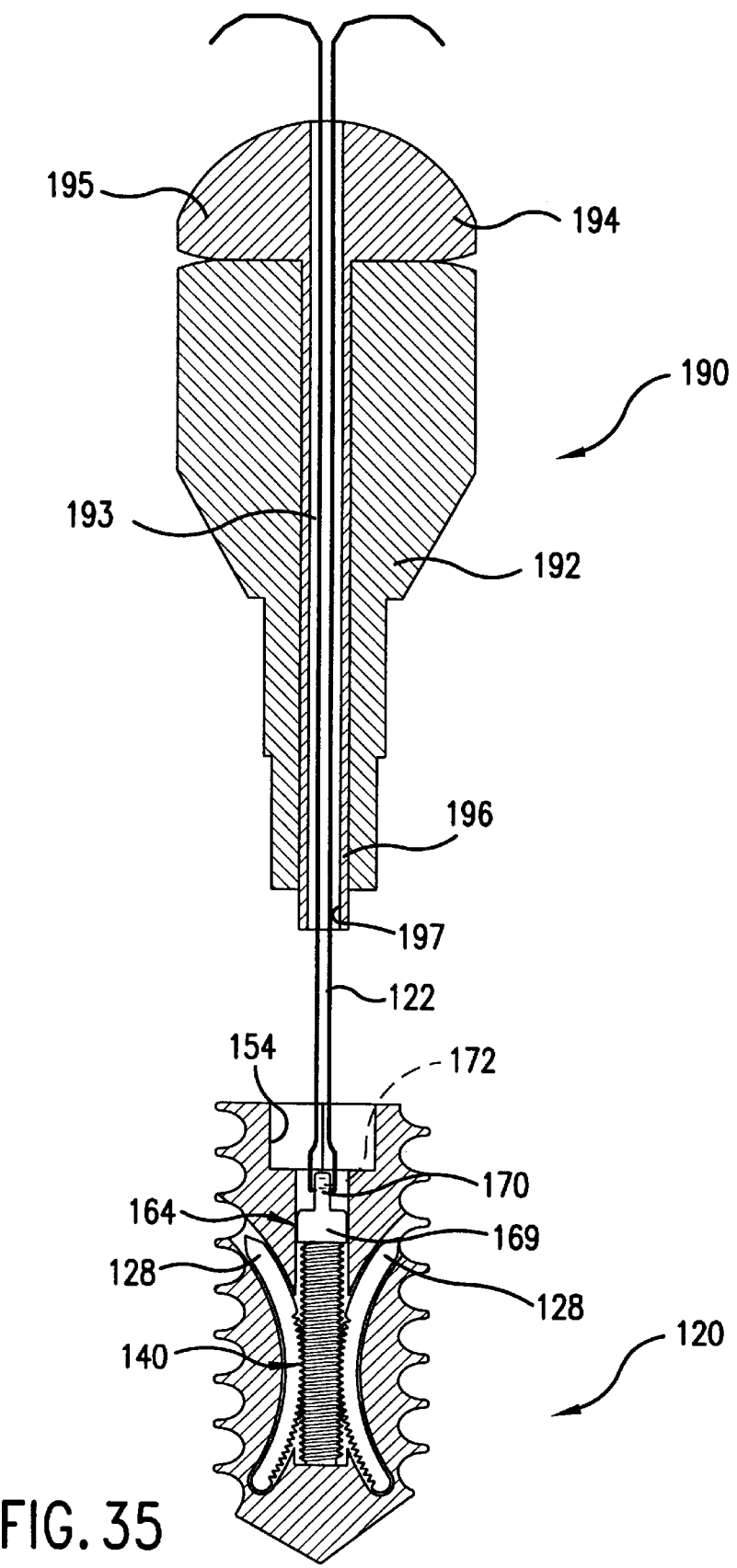
FIG. 35 is a longitudinal sectional view of the tool and surgical anchor showing the suture-like material passing endwise through the tool.

In the illustrated embodiment, and as best shown in FIG. 35, tool 190 is configured as a two part cannulated screw driver. A first or lower part 192 of tool 190 has an elongated hollow configuration defining a central or axial bore 193 extending the length thereof. A lower distal end of the lower part 192 of tool 190 has an exterior configuration that generally corresponds to the configuration of the socket-like opening 154 in the insert 126 whereby turning movements imparted to the lower part 192 of tool 190 will likewise be imparted to the surgical insert 120 as long as the lower portion 192 of tool 190 remains operably engaged with the insert 126.

An upper or second part 194 comprises the remainder of the tool 190. As shown in FIG. 35, the second part 194 of tool 190 includes a handle portion 195 and an elongated tube 196 rigidly connected to the handle portion 195. In the illustrated embodiment, the elongated tube 196 extends axially and rotatably through and beyond the lower end of part 192 of tool 190. The tube-like configuration 196 defines an elongated bore or passage 197 opening to opposite ends of tool 190 for allowing suture-like material 122 therethrough. Notably, the handle portion 195 and the tube 196 connected thereto turn independently of the first or lower portion 192 of tool 190. Returning to FIG. 34, the lower or distal end of tube 196 is configured to releasably engage the axial projection 170 on the driver 164. In the illustrated embodiment, the distal end of the tube 196 has a vertical slot 198 that releasably fits over and about the blade-like projection 170 axially extending from the head portion 169 of the drive member 166 of driver 164.

After the insert 126 is inserted into the bone, mechanism 140 is operated to positively distend the pins 128 radially outwardly to thereby enhance securement of the surgical anchor 120 within the bone. In the illustrated embodiment, when the tool 190 is arranged in operable association with the surgical anchor 120 the second part 194 of the tool 190 is operably engaged with the head portion 169 of the drive member 166 of driver 164 of mechanism 140.

As will be appreciated from an understanding of the structure of tool 190, the second portion 194 of tool 190 is independently operable relative the remainder of the tool 190. As such, turning movements can be imparted to the driver 164 of mechanism 140 independent of and without effecting turning or rotation of the insert 126 of surgical anchor 120. The turning movements imparted to driver 164 of mechanism 140 will result in positive endwise displacement of the pins 128 relative to the insert 126 as through the threaded engagement between the driver 164 and the slanted serrations or threads 178 on the pins 128.

In the illustrated form of mechanism 140, after the pins 128 are extended into the bone substance to thereby secure the surgical anchor 20 within the bone, a lengthwise portion of each pin 128 remains operably associated with the driver 164 of mechanism 140 such that reverse rotation of the driver 164 will positively effect retraction of the pins 128 relative to the insert 126.

Notably, when the surgical anchor 120 is initially positioned within the bone substance, suture-like material 122 is passed through the aperture 172 (FIG. 35) in the head portion 169 of the driver 164 of mechanism 140. The free ends of the suture-like material 122 are threaded through the tube-like part 196 of the second part 194 of the tool 190. As shown in FIG. 35, the free ends of the suture-like material 122 pass endwise through extend outwardly from the proximal end of the tool 190. After the tool 190 is removed from engagement with the surgical anchor 120, the free ends of the suture-like material 122 serve to connect an object such as a ligament or tendon to the trailing end of the surgical anchor 120.

Regardless of which embodiment of the invention is utilized a salient feature of the present invention concerns the provision of a mechanism arranged in operable association with a surgical anchor for effecting positive displacement of pins or barbs relative to the anchor. An important aspect of the present invention concerns the ability to move the pins positively outwardly through manual manipulation of the drive mechanism. Moreover, because the pins remain operably associated with the drive mechanism, should it become necessary or desired to remove the anchor, the drive mechanism can be reversed thereby effecting positive retraction of the pins relative to the anchor thereby facilitating removal of the surgical anchor from the bone.

From the foregoing, it will be observed that numerous modifications and variations can be effected without departing from the true spirit and scope of the novel concept of the present invention. It will be appreciated that the present disclosure is intended to set forth exemplifications of the invention, which are not intended to limit the invention to the specific embodiments illustrated. The disclosure is intended to cover by the appended claims all such modifications as fall within the scope of the claims.

What is claimed is:

1. A surgical anchor comprising:
   an insert having external threading for anchoring said insert into a bone, said insert defining an axially elongated bore opening to a trailing end of said insert, said insert further defining a series of openings between opposite ends of said insert, each opening being configured to intersect with said bore between opposite ends thereof and has one end that opens to an exterior of said insert;
   a series of pins configured for endwise reception and movement within said series of openings defined by said insert such that a lengthwise portion of each pin passes through said bore and moves between a retracted position, wherein said pins have substantially no operable anchoring effect, and an extended position, wherein said pins extend outwardly from said insert to significantly enhance the securement of said insert within said bone; and
   a driver arranged for turning movement within said bore and which is operably associated with each pin wherein said driver includes an axially elongated member with leading and trailing ends and external threading extending between the opposite ends thereof and whereby turning movement of said driver positively causes endwise displacement of said pins within their respective openings and radially relative to said insert as a function of the direction of rotation of said driver.

2. The surgical anchor according to claim 1 wherein said insert is configured toward a trailing end thereof to releasably accommodate a driving tool.

3. The surgical anchor according to claim 1 wherein a leading end of said insert is generally pointed to facilitate insertion and self-tapping of the insert into said bone.

4. The surgical anchor according to claim 1 wherein the trailing end of said member comprising said driver is configured to releasably accommodate a driving tool for imparting turning movements to said member.

5. A surgical anchor comprising:
   an insert having external threading for anchoring said insert into a bone, said insert defining an axially elongated bore opening to a trailing end of said insert, said insert further defining a series of openings between opposite ends of said insert, each opening being configured to intersect with said bore between opposite ends thereof and has one end that opens to an exterior of said insert;
   a series of pins configured for endwise reception and movement within said series of openings defined by said insert such that a lengthwise portion of each pin passes through said bore and moves between a retracted position, wherein said pins have substantially no operable anchoring effect and an extended position, wherein said pins extend outwardly from said insert to significantly enhance the securement of said insert within said bone;
   a driver arranged for turning movement within said bore and which is operably associated with each pin whereby turning movement of said driver positively causes endwise displacement of said pins within their respective openings and radially relative to said insert as a function of the direction of rotation of said driver; and
   a ligament anchor extending beyond and connected to the trailing end of said insert for allowing a lengthwise portion of suture-like material to be connected to the insert.

6. A surgical anchor comprising:
   an insert having external threading for anchoring said insert into a bone, said insert defining an axially elongated bore opening to a trailing end of said insert wherein the trailing end of said insert is configured to allow a lengthwise portion of suture-like material to be connected to the insert, said insert further defining a series of openings between opposite ends of said insert, each opening being configured to intersect with said bore between opposite ends thereof and has one end that opens to an exterior of said insert;
   a series of pins configured for endwise reception and movement within said series of openings defined by said insert such that a lengthwise portion of each pin passes through said bore and moves between a retracted position, wherein said pins have substantially no operable anchoring effect, and an extended position, wherein said pins extend outwardly from said insert to significantly enhance the securement of said insert within said bone; and
   a driver arranged for turning movement within said bore and which is operably associated with each pin whereby turning movement of said driver positively causes endwise displacement of said pins within their respective openings and radially relative to said insert as a function of the direction of rotation of said driver.

7. A surgical anchor comprising:
   an insert having external threading for anchoring said insert into a bone, said insert defining an axially elongated bore opening to a trailing end of said insert wherein the bore of said insert is configured with a blind cavity portion arranged toward one end thereof and an internally threaded portion arranged in axially adjacent relation relative to each other, said insert further defining a series of openings between opposite ends of said insert, each opening being configured to intersect with said bore between opposite ends thereof and has one end that opens to an exterior of said insert;
   a series of pins configured for endwise reception and movement within said series of openings defined by said insert such that a lengthwise portion of each pin passes through said bore and moves between a retracted position, wherein said pins have substantially no operable anchoring effect, and an extended position, wherein said pins extend outwardly from said insert to significantly enhance the securement of said insert within said bone; and
   a driver arranged for turning movement within said bore and which is operably associated with each pin whereby turning movement of said driver positively causes endwise displacement of said pins within their respective openings and radially relative to said insert as a function of the direction of rotation of said driver.

8. The surgical anchor according to claim 7 wherein the series of openings in the insert intersect with the blind cavity portion of said bore.

9. The surgical anchor according to claim 7 wherein said driver is arranged for free turning movement with respect to said insert within the blind cavity portion of the bore of said insert.

10. The surgical anchor according to claim 7 further including a ligament anchor extending beyond and threadably connected to the internal threaded portion of the bore defined by said insert for allowing a lengthwise portion of suture-like material to be connected to the insert.

11. The surgical anchor according to claim 10 wherein said ligament anchor comprises a threaded shank portion having external threading for permitting said ligament anchor to be releasably connected to the insert and an enlarged and apertured head portion at the trailing end, the apertures in said head portion permitting suitable attachment of a ligament to said surgical anchor.

12. A surgical anchor comprising:
an axially elongated bone screw defining an elongated axis and having external threading axially extending from a leading end of said screw for anchoring said screw into a bone, said screw defining an elongated bore opening to a trailing end of said screw wherein the bore in said screw is configured with a blind cavity portion arranged toward the leading end of said screw and extending for an axial distance along said axis and an internally threaded portion that opens to said blind cavity and to the trailing end of said screw, and a series of openings equally disposed about said axis each opening being configured to intersect with said bore between opposite ends thereof and has one end that opens to an exterior of said screw;
a series of elongated pins configured for endwise reception and movement within said series of openings defined by said screw such that a lengthwise portion of each pin passes proximate to said elongated axis and moves between a retracted position, wherein said pins have substantially no operable anchoring effect, and an extended position, wherein said pins radially extend outwardly from said screw to significantly enhance the anchorage of said screw within said bone; and
a mechanism carried by said screw for movement within said bore, said mechanism being operably associated with each pin such that movements imparted to said mechanism causes endwise displacement of said pins within their respective openings and outwardly relative to said screw as a function of the movement of said mechanism.

13. The surgical anchor according to claim 12 wherein each pin has a slanted serrated configuration between opposite ends thereof.

14. The surgical anchor according to claim 12 wherein a trailing end of said axial bore defined by said screw is configured to releasably accommodate a driving tool for imparting turning movement to the screw.

15. The surgical anchor according to claim 12 further including a ligament anchor extending beyond and threadably connected to the internally threaded portion of the bore defined by said screw for allowing a lengthwise portion of suture-like material to be connected to the screw.

16. The surgical anchor according to claim 15 wherein said ligament anchor is formed from a material chosen from the class comprised of: titanium, a titanium alloy, stainless steel, or cobalt chromium alloy.

17. The surgical anchor according to claim 15 wherein said ligament anchor comprises a threaded shank portion having external threading for permitting said anchor to be releasably connected to the screw and an enlarged and apertured head portion at the trailing end of said anchor, the apertured head portion of said ligament anchor permitting attachment of a ligament to said anchor.

18. The surgical anchor according to claim 12 wherein the trailing end of the screw is configured to releasably accommodate a driving tool for imparting turning movement to the screw.

19. The surgical anchor according to claim 12 wherein an open end of the bore defined by said screw is configured as a socket to releasably accommodate a driving tool therewithin.

20. The surgical anchor according to claim 12 wherein said screw is formed from a material compatible with the bone into which the screw is inserted.

21. The bone screw assembly according to claim 20 wherein said screw is formed of a material from the class including: titanium, a titanium alloy, cobalt chromium alloy, or stainless steel.

22. The bone screw assembly according to claim 12 wherein said pins are formed from a material compatible with human bone tissue.

23. The bone screw assembly according to claim 22 wherein said pins are formed of a material from the class of: titanium, a titanium alloy, a cobalt chromium alloy, or stainless steel.

24. A surgical anchor comprising:
an axially elongated bone screw defining an elongated axis and having external threading axially extending from a leading end of said screw for anchoring said screw into a bone, said screw defining an elongated bore opening to a trailing end of said screw wherein the trailing end of said screw is configured to allow a lengthwise segment of suture-like material to be connected to the screw, and a series of openings equally disposed about said axis, each opening being configured to intersect with said bore between opposite ends thereof and has one end that opens to an exterior of said screw;
a series of elongated pins configured for endwise reception and movement within said series of openings defined by said screw such that a lengthwise portion of each pin passes proximate to said elongated axis and moves between a retracted position, wherein said pins have substantially no operable anchoring effect, and an extended position, wherein said pins radially extend outwardly from said screw to significantly enhance the anchorage of said screw within said bone; and
a mechanism carried by said screw for movement within said bore said mechanism being operably associated with each pin such that movements imparted to said mechanism causes endwise displacement of said pins within their respective openings and outwardly relative to said screw as a function of the movement of said mechanism.

25. A surgical anchor comprising:
an axially elongated bone screw defining an elongated axis and having external threading axially extending from a leading end of said screw for anchoring said screw into a bone, said screw defining an elongated bore opening to a trailing end of said screw, and a series of openings equally disposed about said axis, each opening being configured to intersect with said bore between opposite ends thereof and has one end that opens to an exterior of said screw;
a series of elongated pins configured for endwise reception and movement within said series of openings defined by said screw such that a lengthwise portion of each pin passes proximate to said elongated axis and moves between a retracted position, wherein said pins have substantially no operable anchoring effect, and an extended position, wherein said pins radially extend outwardly from said screw to significantly enhance the anchorage of said screw within said bone;

a mechanism carried by said screw for movement within said bore, said mechanism being operably associated with each pin such that movements imparted to said mechanism causes endwise displacement of said pins within their respective openings and outwardly relative to said screw as a function of the movement of said mechanism; and a ligament anchor extending beyond and connected to the trailing end of the screw for allowing a lengthwise segment of suture-like material to be connected to the screw.

26. A surgical anchor adapted for insertion within a bone of a patient, said surgical anchor comprising:

an elongated insert formed of a material compatible with human bone and tissue;

a series of fasteners carried by, but not integral with, said insert for movement between retracted and extended positions, wherein when said fasteners are in said retracted position said fasteners offer substantially no operable anchoring effect to said insert relative to said bone, and wherein when said fasteners are in their extended position they extend outwardly from said insert while remaining in operable combination therewith to secure said insert within said bone; and a mechanism arranged in operable combination with and for positively moving said fasteners between said retracted and said extended position and for positively moving said fasteners from said extended position to said retracted position, said mechanism comprising a driver mounted for free rotation in a cavity defined by said insert, said driver having external threading for engaging with slanted serrations on each of said fasteners whereby each fastener is endwise and positively displaced in either direction of travel upon and as a function of turning movements being imparted to said driver.

27. The surgical anchor according to claim 26 wherein said insert is configured toward one end to allow a portion of suture-like material to be fastened to said surgical anchor thereby allowing an object to be connected with said suture-like material to said one end of said surgical anchor.

28. The surgical anchor according to claim 26 wherein said insert is formed from a material chosen from a class comprised of: titanium, a titanium alloy, stainless steel, or a cobalt chromium alloy.

29. The surgical insert according to claim 26 wherein each fastener in said series of fasteners is formed from a material chosen from a class comprised of: titanium, a titanium alloy, stainless steel, or a cobalt chromium alloy.

30. The surgical anchor according to claim 26 wherein each fastener in said series of fasteners is carried by said insert for endwise displacement between said extended and retracted positions.

31. The surgical anchor according to claim 26 further including a ligament anchor connected to an end region of said insert for allowing a segment of suture-like material to be connected thereby allowing an object to be connected to the surgical anchor with said suture-like material.

32. The surgical anchor according to claim 26 wherein said insert includes external threading axially extending from a leading end for enhancing securement of said surgical anchor in the bone.

33. The surgical anchor according to claim 32 wherein a trailing end of said insert is configured to releasably accommodate a driving tool capable of imparting turning movements to said insert.

34. The surgical anchor according to claim 26 wherein each fastener has an arcuate configuration between opposite ends thereof.

35. The surgical anchor according to claim 26 wherein said fasteners are equally disposed about and relative to a longitudinal axis of said insert.

36. The surgical anchor according to claim 26 wherein said insert defines a plurality of elongated channels, each channel having a blind forward end and an opposite end opening to the periphery of said insert.

37. The surgical anchor according to claim 36 wherein said channels are located in equally spaced relation relative to each other and about said insert.

38. The surgical anchor according to claim 36 wherein each channel has an arcuate configuration between opposite ends thereof.

39. A surgical anchor for attaching an object to a bone of a patient, said surgical anchor comprising:

an elongated insert having a first end adapted for longitudinal insertion into said bone and a second end;

pins carried by, but not integral with, said insert for endwise movement between retracted and extended positions, wherein when said pins are in said retracted positions they offer substantially no operable anchoring effect to said bone, and wherein when said pins are in said extended positions they radially extend outwardly from said insert while remaining in operable association therewith to secure said insert within said bone; and a mechanism for positively moving said pins endwise relative to said insert between said extended and retracted positions, said mechanism comprising a driver mounted for free rotation in a cavity defined by said insert said driver having external threading for engaging with slanted serrations on each of said pins whereby each pin is endwise and positively displaced in either direction of travel upon and as a function of turning movements being imparted to said driver.

40. The surgical anchor according to claim 39 wherein said insert is configured toward said second end to allow a portion of suture-like material to be fastened to said anchor thereby allowing said object to be connected with said suture-like material to a distal end of said anchor.

41. The surgical anchor according to claim 39 wherein said insert is formed from a material chosen from a class comprised of: titanium, a titanium alloy, stainless steel, or a cobalt chromium alloy.

42. The surgical fastener according to claim 39 wherein each pin is formed from a material chosen from a class comprised of: titanium, a titanium alloy, stainless steel, or a cobalt chromium alloy.

43. The surgical anchor according to claim 39 wherein each pin has an arcuate configuration between opposed ends thereof.

44. The surgical anchor according to claim 39 further including a ligament anchor connected to an end region of said insert for allowing a segment of suture-like material to be connected thereto thereby allowing said object to be connected to the anchor with said suture-like material.

45. The surgical anchor according to claim 39 wherein said insert includes external threading axially extending from said first end for enhancing securement of said surgical anchor in the bone.

46. The surgical anchor according to claim 45 wherein said second end of said insert is configured to releasably accommodate a driving tool capable of imparting turning movements to said insert.

47. The surgical anchor according to claim 39 wherein each pin is configured at a free end thereof to facilitate insertion within bone substance upon distention of said pins relative to said insert.

48. The surgical anchor according to claim 39 wherein said pins are equally disposed about and relative to the longitudinal axis of said insert.

49. The surgical anchor according to claim 39 wherein said insert defines a plurality of elongated channels, each channel having a blind forward end and an opposite end opening to the periphery of said insert.

50. The surgical anchor according to claim 49 wherein said channels are located in equally spaced relation relative to each other and about said insert.

51. The surgical anchor according to claim 49 wherein each channel has an arcuate configuration between opposite ends thereof.

* * * * *